(12) United States Patent
Barnidge et al.

(10) Patent No.: US 10,955,420 B2
(45) Date of Patent: Mar. 23, 2021

(54) IDENTIFICATION AND MONITORING OF CLEAVED IMMUNOGLOBULINS BY MOLECULAR MASS

(71) Applicant: Mayo Foundation for Medical Education and Research, Rochester, MN (US)

(72) Inventors: David R. Barnidge, Rochester, MN (US); David L. Murray, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/331,228

(22) PCT Filed: Sep. 7, 2017

(86) PCT No.: PCT/US2017/050430
§ 371 (c)(1),
(2) Date: Mar. 7, 2019

(87) PCT Pub. No.: WO2018/049001
PCT Pub. Date: Mar. 15, 2018

(65) Prior Publication Data
US 2019/0195888 A1   Jun. 27, 2019

Related U.S. Application Data

(60) Provisional application No. 62/384,445, filed on Sep. 7, 2016.

(51) Int. Cl.
*G01N 33/68* (2006.01)
*C12Q 1/37* (2006.01)
*G01N 30/72* (2006.01)

(52) U.S. Cl.
CPC .......... *G01N 33/6848* (2013.01); *C12Q 1/37* (2013.01); *G01N 30/72* (2013.01); *G01N 33/6857* (2013.01); *G01N 33/6893* (2013.01); *G01N 2333/96433* (2013.01); *G01N 2800/101* (2013.01); *G01N 2800/102* (2013.01); *G01N 2800/104* (2013.01); *G01N 2800/24* (2013.01); *G01N 2800/26* (2013.01); *G01N 2800/52* (2013.01); *G01N 2800/7095* (2013.01)

(58) Field of Classification Search
CPC .......... C12Q 1/37; G01N 2333/96433; G01N 2800/101; G01N 2800/102; G01N 2800/104; G01N 2800/24; G01N 2800/26; G01N 2800/52; G01N 2800/7095; G01N 30/72; G01N 33/6848; G01N 33/6857; G01N 33/6893
See application file for complete search history.

(56) References Cited

U.S. PATENT DOCUMENTS

| | | |
|---|---|---|
| 8,501,907 B2 | 8/2013 | Jordan et al. |
| 8,679,767 B2 | 3/2014 | Kaur et al. |
| 2002/0182649 A1 | 12/2002 | Weinberger et al. |
| 2003/0027216 A1 | 2/2003 | Kiernan et al. |
| 2005/0009009 A1 | 1/2005 | Peiris et al. |
| 2005/0064422 A1 | 3/2005 | Barnidge et al. |
| 2006/0024296 A1 | 2/2006 | Williams et al. |
| 2006/0281122 A1 | 12/2006 | Bryant |
| 2007/0015222 A1 | 1/2007 | Kaneko et al. |
| 2007/0054407 A1 | 3/2007 | Chen et al. |
| 2007/0105181 A1 | 5/2007 | Pope et al. |
| 2007/0184470 A1 | 8/2007 | Arman et al. |
| 2007/0259398 A1 | 11/2007 | Arnott et al. |
| 2007/0292441 A1 | 12/2007 | Glover et al. |
| 2008/0026949 A1 | 1/2008 | Hoidal et al. |
| 2008/0064055 A1 | 3/2008 | Bryant |
| 2008/0142696 A1 | 6/2008 | Geromanos et al. |
| 2008/0171312 A1 | 7/2008 | Ley et al. |
| 2008/0317745 A1 | 12/2008 | Boruchov et al. |
| 2009/0155280 A1* | 6/2009 | Jordan .............. A61P 43/00 424/139.1 |
| 2009/0186423 A1 | 7/2009 | Frandsen |
| 2009/0203602 A1 | 8/2009 | Gelber et al. |
| 2009/0258828 A1 | 10/2009 | Beuerman et al. |
| 2010/0015652 A1 | 1/2010 | Granda et al. |
| 2010/0086922 A1 | 4/2010 | Bryant |
| 2010/0167267 A1 | 7/2010 | Schulzknappe et al. |
| 2010/0190652 A1 | 7/2010 | Nagalla et al. |
| 2010/0323381 A1 | 12/2010 | Bergen, III et al. |
| 2011/0065199 A1 | 3/2011 | Kuge et al. |
| 2011/0117021 A1 | 5/2011 | Smith et al. |

(Continued)

FOREIGN PATENT DOCUMENTS

| | | |
|---|---|---|
| EP | 1329719 | 7/2003 |
| EP | 3270154 | 1/2018 |

(Continued)

OTHER PUBLICATIONS

Aisina et al. Structure and Function of Plasminogen/Plasmin System. Russian Journal of Bioorganic Chemistry, 2014, vol. 40, No. 6, pp. 590-605. (Year: 2014).*
Fan et al. A single proteolytic cleavage within the lower hinge of trastuzumab reduces immune effector function and in vivo efficacy. Breast Cancer Research 2012, vol. 14, pp. 1-13. (Year: 2012).*
Dada et al. High-Resolution Capillary Zone Electrophoresis with Mass Spectrometry Peptide Mapping of Therapeutic Proteins: Peptide Recovery and Post-translational Modification Analysis in Monoclonal Antibodies and Antibody-Drug Conjugates. Anal. Chem. 2017, vol. 89, pp. 11236-11242. (Year: 2017).*
Remily-Wood et al. Quantification of Peptides from Immunoglobulin Constant and Variable Regions by Liquid Chromatography—Multiple Reaction Monitoring Mass Spectrometry for Assessment of Multiple Myeloma Patients. Proteomics Clin Appl. Oct. 2014. ; 8(0), pp. 783-795. (Year: 2014).*

(Continued)

*Primary Examiner* — Marcela M Cordero Garcia
(74) *Attorney, Agent, or Firm* — Fish & Richardson P.C.

(57) ABSTRACT

This document relates to materials and methods for identifying and monitoring immunoglobulin cleavage (e.g., IgG cleavage) in a sample, such as a biological sample, using mass spectrometry techniques.

17 Claims, 8 Drawing Sheets

Specification includes a Sequence Listing.

(56) References Cited

U.S. PATENT DOCUMENTS

| | | | |
|---|---|---|---|
| 2011/0151494 A1 | 6/2011 | Koomen et al. |
| 2011/0183426 A1 | 6/2011 | Chan et al. |
| 2011/0294150 A1 | 12/2011 | Koll et al. |
| 2012/0309040 A1 | 12/2012 | Madian et al. |
| 2012/0315645 A1 | 12/2012 | Kaur et al. |
| 2012/0322073 A1 | 12/2012 | Lopez-Girona |
| 2013/0040851 A1 | 2/2013 | Hanzawa et al. |
| 2013/0149389 A1 | 6/2013 | Flora et al. |
| 2013/0178370 A1 | 7/2013 | Lavnder et al. |
| 2013/0178385 A1 | 7/2013 | Bahn et al. |
| 2013/0185096 A1 | 7/2013 | Giusti |
| 2013/0260406 A1 | 10/2013 | Koomen et al. |
| 2014/0045276 A1 | 2/2014 | Singh et al. |
| 2014/0186332 A1 | 7/2014 | Ezrin et al. |
| 2014/0242072 A1 | 8/2014 | Hansson |
| 2014/0242624 A1 | 8/2014 | Valliere-Douglass |
| 2014/0249049 A1 | 9/2014 | Stoll et al. |
| 2015/0204884 A1 | 7/2015 | Robblee |
| 2015/0219665 A1 | 8/2015 | Chapple et al. |
| 2015/0276771 A1 | 10/2015 | Madasamy |
| 2015/0340219 A1 | 11/2015 | Mellors |
| 2015/0362506 A1 | 12/2015 | Zhu et al. |
| 2016/0033511 A1 | 2/2016 | Pannell et al. |
| 2016/0041184 A1 | 2/2016 | Barnidge et al. |
| 2016/0047819 A1 | 2/2016 | Viscom et al. |
| 2016/0206660 A1 | 7/2016 | Shi et al. |
| 2016/0231329 A1 | 8/2016 | Olsson et al. |
| 2016/0257763 A1 | 9/2016 | Von Kreudenstein et al. |
| 2016/0349269 A1 | 12/2016 | Hunt et al. |
| 2017/0023584 A1 | 1/2017 | Murray et al. |
| 2017/0044608 A1 | 2/2017 | Wang et al. |
| 2017/0205423 A1 | 7/2017 | Higel et al. |
| 2017/0336419 A1 | 11/2017 | Tran et al. |
| 2018/0106815 A1 | 4/2018 | Barnidge et al. |
| 2018/0267057 A1 | 9/2018 | Barnidge et al. |
| 2019/0195888 A1 | 6/2019 | Barnidge et al. |
| 2020/0003784 A1 | 1/2020 | Murray et al. |

FOREIGN PATENT DOCUMENTS

| | | |
|---|---|---|
| SG | 183701 | 9/2012 |
| WO | WO 2005/101017 | 10/2005 |
| WO | WO 2008/057083 | 12/2006 |
| WO | WO 2006138629 | 12/2006 |
| WO | WO 2010/119295 | 10/2010 |
| WO | WO 2011/077129 | 6/2011 |
| WO | WO 2012/056232 | 5/2012 |
| WO | WO 2013/049410 | 4/2013 |
| WO | WO 2013096451 | 6/2013 |
| WO | WO 2013/185180 | 12/2013 |
| WO | WO 2014/078374 | 5/2014 |
| WO | WO 2014/105985 | 7/2014 |
| WO | WO 2014109927 | 7/2014 |
| WO | WO 2014/121031 | 8/2014 |
| WO | WO 2014150170 | 9/2014 |
| WO | WO 2015/131169 | 9/2015 |
| WO | WO 2015154052 | 10/2015 |
| WO | WO 2016018978 | 2/2016 |
| WO | WO 2016/134365 | 8/2016 |
| WO | WO 2016/172485 | 10/2016 |
| WO | WO 2017022315 | 2/2017 |
| WO | WO 2017/134274 | 8/2017 |
| WO | WO 2017/144903 | 8/2017 |
| WO | WO 2017/180735 | 10/2017 |
| WO | WO 2017/205694 | 11/2017 |
| WO | WO 2018/049001 | 3/2018 |

OTHER PUBLICATIONS

Abca3:74m, "Understanding secondary antibodies" 2012, 12 pages, downloaded from http://docs.abcam.com/pdf/general/understanding_secondary_antibodies.pdf.

Abraham et al., "Characterization of free immunoglobulin light chains (LC) by mass spectrometry in light chain-associated (AL) amyloidosis," American Society of Hematology 43rd Annual Meeting, part 2, Orlando, Florida, USA, 98(11 Pt 2), p. 31b, Abstract#3722, Nov. 16, 2001.

Abraham et al., "Correlation of serum immunoglobulin free light chain quantification with urinary Bence Jones protein in light chain myeloma," Clin. Chem., 48(4):655-657, Apr. 2002.

Abraham et al., "Trimolecular complexes of lambda light chain dimers in serum of a patient with multiple myeloma," Clin Chem., 48(10):1805-1811, Oct. 2002.

Adamczyk et al., "Profiling of polyclonal antibody light chains by liquid chromatography/electrospray ionization mass spectrometry," Rapid Commun Mass Spectrom., 14:49-51, 2000.

Adamczyk et al.,"Papain digestion of different mouse IgG subclasses as studied by electrospray mass spectrometry," J Immun Methods., 237:95-104, 2000.

Alge et al., "Proteomic Analysis of Plasma Exosome-Associated Proteins Reveals That Differences in Kappa: Lambda Ratios Predict Severe Acute Graft-Versus-Host Disease Early After Allogeneic Hematopoietic Stem Cell Transplantation," Blood., 1278, Nov. 2010.

Alldridge et al., "Proteome profiling of breast tumors by gel electrophoresis and nanoscale electrospray ionization mass spectrometry," J. Proteome. Res., 7(4):1458-1469, Apr. 2008.

Anonymous: "KappaSelect LambdaFabSelect," Data File 28-9448-22 AB, Mar. 1, 2012, Retrieved from the Internet: URL: https://www.gelifesciences.co.jp/catalog/pdf/Kappaselect_LamdaFabSelect.pdf Retrieved on Sep. 22, 2017, 4 pages.

Arun et al., "Immunohistochemical examination of light-chain expression (lambda/kappa ratio) in canine, feline, equine, bovine and porcine plasma cells," Zentralbl Veterinarmed A., 43(9):573-576, Nov. 1996.

Aucouturier et al., "Monoclonal Ig L chain and L chain V domain fragment crystallization in myeloma-associated Fanconi's syndrome" J. Immunol., 150(8 Pt 1):3561-3568, Apr. 1993.

Aucouturier et al., "Monoclonal immunoglobulin light chains associated to Fanconi's syndrome," Monoclonal Gammopathies and the Kidney, 2003, 87-92.

Awad et al., "Analyses of cerebrospinal fluid in the diagnosis and monitoring of multiple sclerosis," J Neuroimmunol., 219(1-2):1-7, Epub Sep. 25, 2009.

Barnidge and Murray, "Using Mass Spectrometry to Identify IgG Fc and Fab Fragments Produced by Plasmin in Patient Serum," Poster, Presented at American Society for Mass Spectrometry meeting on Jun. 7, 2016.

Barnidge et al., "Monitoring free light chains in serum using mass spectrometry," Clinical Chemistry and Laboratory Medicine (CCLM). ISSN (Online) 1437-4331, ISSN (Print) 1434-6621, DOI: 10.1515/cclm-2015-0917, Feb. 2016.

Barnidge et al., "Monitoring M-proteins in patients with multiple myeloma using heavy-chain variable region clonotypic peptides and LC-MS/MS," J Proteome Res., 13(4):1905-1910, Epub Mar. 5, 2014.

Barnidge et al., "Phenotyping polyclonal kappa and lambda light chain molecular mass distributions in patient serum using mass spectrometry," J Proteome Res., 13(11):5198-5205, Epub Aug. 26, 2014.

Barnidge et al., "Using MALDI-TOF MS to Screen for Monoclonal Gammopathies in Serum and Urine," 61st Annual ASMS Conference on Mass Spectrometry and Allied Topics, Minneapolis, MN, Jun. 9-13, 2013, 1 page poster.

Barnidge et al., "Using mass spectrometry to monitor monoclonal immunoglobulins in patients with a monoclonal gammopathy," J Proteome Res., 13(3):1419-1427, Epub Feb. 11, 2014.

Barnidge, "Monitoring specific IgG tryptic peptides in multiple myeloma using the TripleTOFtm 5600 System," AB SCIEX Annual Users Meeting at ASMS, May 20, 2012, 28 slides.

Barratt et al., "Urine proteomics: the present and future of measuring urinary protein components in disease," CMAJ, 177(4):361-368, Aug. 2007.

Bastian et al., "Intra- and interchain disulfide bridges of the human J chain in secretory immunoglobulin A," Biol. Chem. Hoppe Seyler., 373(12):1255-63, Dec. 1992.

(56) References Cited

OTHER PUBLICATIONS

Beck et al., "Characterization of therapeutic antibodies and related products," Anal. Chem., 85(2):715-736, Jan. 2013.
Bennett et al., "Monitoring papain digestion of a monoclonal antibody by electrospray ionization mass spectrometry," Analytical Biochemistry., 245:17-27,1997.
Berg et al., "Mass spectrometry based proteomic analysis identifies two distinct types of cutaneous amyloidosis," Mod Pathol., vol. 22; p100A, 2009.
Bergen et al., "Characterization of amyloidogenic immunoglobulin light chains directly from serum by on-line immunoaffinity isolation," Biomedical Chromatography, 18(3):191-201, Apr. 1, 2004.
Bergon et al., "Linearity and detection limit in the measurement of serum M-protein with the capillary zone electrophoresis system Capillarys," Clinical Chemistry and Laboratory Medicine, 43:721-723, 2005.
Bermudez-Crespo et al., "A better understanding of molecular mechanisms underlying human disease," Proteomics Clinical Applications, 1:983-1003, 2007.
Biosis accession No. PREV200200151435, 2 pages, Nov. 2001 Abstract only.
Biosis accession No. PREV201100424453, 2 pages, Nov. 2010 Abstract only.
Bois et al., "Cutaneous amyloidosis: mass spectrometry based proteomic analysis reveals diverse etiology associated with unique histopathological features," Mod Pathol., 26:320A-321A, Feb. 2013.
Boissinot et al., "Up-Regulation of Anti-Inflammatory, STAT3-Activating Hepatocyte Growth Factor and Interleukin-11 in Polycythemia Vera Is Independent of JAK2V617F and Contributes to the Growth of Clonal Erythroblasts," Blood, 116(21):796, Nov. 2010, 52nd Annual Meeting of the American Society of Hematology, Orlando, FL, USA Dec. 4-7, 2010.
Bondarenko et al., "Mass measurement and top-down HPLC/MS analysis of intact monoclonal antibodies on a hybrid linear quadrupole ion trap-orbitrap mass spectrometer," J Am Soc Mass Spectrometry., 20:1415-1424, 2009.
Bourell et al., "Electrospray ionization mass spectrometry of recombinantly engineered antibody fragments," Anal Chem., 66:2088-2095, 1994.
Bradwell et al., "Highly sensitive, automated immunoassay for immunoglobulin free light chains in serum and urine," Clin Chem., 47(4):673-680, Apr. 2001.
Breitkopf et al., "Detection of a rare BCR-ABL tyrosine kinase fusion protein in H929 multiple myeloma cells using immunoprecipitation (IP)-tandem mass spectrometry (MS/MS)," Proc. Natl. Acad. Sci. USA., 109(40):16190-16195, Oct. 2012.
Brochet et al., "IMGT/V-QUEST: the highly customized and integrated system for IG and TR standardized V-J and V-D-J sequence analysis," Nucleic Acids Res., 36(Web Server issue):W503-W508, Epub May 24, 2008.
Butler et al., "Immunoglobulins, antibody repertoire and B cell development," Dev Comp Immunol., 33(3):321-333, Epub Sep. 18, 2008.
Chen et al., "Characterization of protein therapeutics by mass spectrometry: recent developments and future directions," Drug Discovery Today., 16:58-64, 2011.
Cheung et al., "A proteomics approach for the identification and cloning of monoclonal antibodies from serum," Nature Biotechnology., 30:447-452, 2012.
Chevreux et al., "Fast analysis of recombinant monoclonal antibodies using IdeS proteolytic digestion and electrospray mass spectrometry," Analytical Biochemistry, 415(2):212-214, Aug. 2011.
Chiasserini et al., "CSF proteome analysis in multiple sclerosis patients by two-dimensional electrophoresis," Eur. J. Neurol., 15(9):998-1001, Sep. 2008.
Chung et al., "Thermodynamic stability of a kappaI immunoglobulin light chain: relevance to multiple myeloma," Biophys. J., 88(6):4232-4242, Jun. 2005.
Cohen., "Antibody structure," J Clin Path., 28 Suppl, 6:1-7, 1975.
Cordoba et al., "Non-enzymatic hinge region fragmentation of antibodies in solution," J Chromatography B., 818:115-121, 2005.
Coriu et al., "A molecular basis for nonsecretory myeloma," Blood, 104(3):829-831, Aug. 2004.
D'Aguanno et al., "Differential cerebrospinal fluid proteome investigation of Leber hereditary optic neuropathy (LHON) and multiple sclerosis," 193(1-2):156-160, Dec. 2007.
Dannoc et al., "High resolution proteome analysis of cryoglobulins using Fourier transform-ion cyclotron resonance mass spectrometry," Proteomics, 3(8):1425-1433, Aug. 2003.
De Costa et al., "Sequencing and Quantifying IgG Fragments and Antigen-Binding Regions by Mass Spectrometry" Journal of Proteome Research, 9:2937-2945, Epub Apr. 14, 2010.
De Lorenzi et al., "Urokinase links plasminogen activation and cell adhesion by cleavage of the RGD motif in vitronectin," EMBO reports, 17(7):982-98, Jul. 2016.
Dear et al., "Acquired dysfibrinogenemia caused by monoclonal production of immunoglobulin lambda light chain," Haematologica., 92(11):e111-7, Nov. 2007.
Dekker et al., "An Antibody-Based Biomamarker Discovery Method by Mass Spectrometry Sequencing of Complementarity Determining Regions," Analytical and Bioanalytical Chemistry, 399:1081-1091, 2011.
Dillon et al., "Optimization of a reversed-phase high-performance liquid chromatography/mass spectrometry method for characterizing recombinant antibody heterogeneity and stability," J. Chromatogr. A., 1120(1-2):112-20, Jul. 2006.
Dogan et al., "Leukocyte Chemotactic Factor 2 Amyloidosis: A Novel Type of Amyloidosis That Mimics AL Amyloidosis," presented at The United States and Canadian Academy of Pathology Annual Meeting, Mar. 2009, 1 page.
Drożdż et al., "Immunoglobulin cleavage by hypochlorous acid treatment," Clinica. Chimica. acta., 236(2):155-60, May 1995.
Faca et al., "Innovative proteomic approaches for cancer biomarker discovery," Biotechniques, 43(3):279-283, Sep. 2007.
Fan et al., "Identification of Niemann-Pick C1 disease biomarkers through sphingolipid profiling," J. Lipid. Res., 54(10):2800-2814, Oct. 2013.
Favereaux et al., "Serum IgG antibodies to P0 dimer and 35 kDa P0 related protein in neuropathy associated with monoclonal gammopathy," J Neurol Neurosurg Psychiatry., 74:1262-1266, 2003.
Fortini et al., "Cerebrospinal fluid oligoclonal bands in the diagnosis of multiple sclerosis. Isoelectric focusing with IgG immunoblotting compared with high-resolution agarose gel electrophoresis and cerebrospinal fluid IgG index," Am J Clin Pathol., 120(5):672-675, Nov. 2003.
Frangione, B., "Structure of Human Immunoglobulins and their Variants" B. Benacerraf (ed) Immunogenetics and Immunodeficiency, 1-53, 1975.
Gadgil et al., "The LC/MS analysis of glycation of IgG molecules in sucrose containing formulations," Journal of Pharmaceutical Sciences, 96(10):2607-2621, Oct. 2007.
Gebski et al., "Affinity chromatography applications with single-domain antibodies," Bioprocess International., Aug. 1, 2013, Retrieved from the Internet: URL: http://www.bioprocessintl.com/2013/affinity-chromatography-applications-with-single-domain-antibodies-345480/ Retrieved on Sep. 22, 2017.
GenBank Accession AAA59107, "immunoglobulin lambda light chain C2 region, partial [Homo sapiens]," May 4, 2000, 2 pages.
Gucinski et al., "Evaluation of intact mass spectrometry for the quantitative analysis of protein therapeutics," Anal. Chem., 84(18):8045-8051, Sep. 2012.
Hagman et al., "Absolute quantification of monoclonal antibodies in biofluids by liquid chromatography-tandem mass spectrometry," Analytical Chemistry, 80(4):1290-1296, Feb. 15, 2008.
Hagmann et al., "Characterization of the F(ab')2 fragment of a murine monoclonal antibody using capillary isoelectric focusing and electrospray ionization mass spectrometry," J Chromatography A., 816:49-58, 1998.
Hanash et al., "Mining the plasma proteome for cancer biomarkers," Nature, 452(7187)571-579, Apr. 2008.

(56) References Cited

OTHER PUBLICATIONS

Haraldsson et al., "Determination of kappa and lambda light chains in serum immunoglobulins G, A and M," Ann Clin Biochem., 28 (Pt 5):461-466, Sep. 1991.
Heudi et al., "Towards absolute quantification of therapeutic monoclonal antibody in serum by LC-MS/MS using isotope-labeled antibody standard and protein cleavage isotope dilution mass spectrometry," Anal Chem., 80(11):4200-4207, Epub May 9, 2008.
Hieter et al., "Clustered arrangement of immunoglobulin constant region genes in man," Nature, 294:536-540, 1981.
Hill et al., "Serum free light chains: an alternative to the urine Bence Jones proteins screening test for monoclonal gammopathies," Clin. Chem., 52(9):1743-1748, Sep. 2006.
Holding et al., "Use of serum free light chain analysis and urine protein electrophoresis for detection of monoclonal gammopathies," Clin. Chem. Lab. Med., 49(1):83-88, Jan. 2011.
Hsieh et al., "Elucidation of potential bortezomib response markers in multiple myeloma patients," Journal of Pharmaceutical and Biomedical Analysis, 49:115-122, 2009.
Huse et al., "Purification of antibodies by affinity chromatography," Journal of biochemical and biophysical methods, 51(3):217-31, May 2002.
International Search Report in International Application No. PCT/US2017/050430 dated Nov. 27, 2017, 5 pages.
Jagannath et al., "Value of serum free light chain testing for the diagnosis and monitoring of monoclonal gammopathies in hematology," Clin Lymphoma Myeloma, 7(8):518-523, Sep. 2007.
Jemal et al., "Cancer statistics, 2003," CA Cancer J Clin., 53(1):5-26, Jan.-Feb. 2003.
Johnson et al., "Cation exchange-HPLC and mass spectrometry reveal C-terminal amidation of an IgG1 heavy chain," Anal. Biochem., 360(1):75-83, Jan. 2007.
Jones et al., "A protocol for 'enhanced pepsin digestion': a step by step method for obtaining pure antibody fragments in high yield from serum," J of Immunol Methods., 275:239-250, 2003.
Joosten et al., "The production of antibody fragments and antibody fusion proteins by yeasts and filamentous fungi," Microbial Cell Factories., 2:1, 15 pages, 2003.
Kabat et al., "An electrophoretic study of the protein components in cerebrospinal fluid and their relationship to the serum proteins," J Clin Invest., 21(5):571-577, Sep. 1942.
Kalaga et al., "Unexpected presence of polyreactive catalytic antibodies in IgG from unimmunized donors and decreased levels in rheumatoid arthritis," J. Immunol., 155(5):2695-2702, Sep. 1995.
Kaltashov et al., "Advances and challenges in analytical characterization of biotechnology products: Mass spectrometry-based approaches to study properties and behavior of protein therapeutics," Biotechnology Advances., 30:210-222, 2012.
Kaplan et al., "Free light chains in plasma of patients with light chain amyloidosis and non-amyloid light chain deposition disease. High proportion and heterogeneity of disulfide-linked monoclonal free light chains as pathogenic features of amyloid disease," British Journal of Haematology., 144(5):705-715, 2008.
Kaplan et al., "Immunoglobulin free light chain dimers in human diseases," The Scientific World Journal, 11:726-735, Mar. 2011.
Kaplan et al., "Isolation and biochemical characterization of plasma monoclonal free light chains in amyloidosis and multiple myeloma: a pilot study of intact and truncated forms of light chains and their charge properties," Clin. Chem. Lab. Med., 46(3):335-341, Mar. 2008.
Katzmann et al., "Serum reference intervals and diagnostic ranges for free kappa and free lambda immunoglobulin light chains: relative sensitivity for detection of monoclonal light chains," Clin. Chem., 48(9):1437-44, Sep. 2002.
Kleennann et al., "Characterization of IgG1 immunoglobulins and peptide-Fc fusion proteins by limited proteolysis in conjunction with LC-MS," Analytical Chemistry, 80(6):2001-2009, Mar. 2008.
Kohlhagen, "Using MALDI-TOF MS to Screen for Monoclonal Proteins in Serum," The Association for Mass Spectrometry Applications to the Clinical Lab [online] 2015. Retrieved from the Internet: <URL: https://www.msacl.org/2015_US_Long_Abstracts/201412041312_53747.pdf>, MSACL 2015 US: Preliminary Conference Program, San Diego, CA, Mar. 28-Apr. 1, 2015, 2 pages.
Koomen et al., "Proteomic contributions to personalized cancer care," Molecular & Cellular Proteomics, 7.10:1780-1794, 2008.
Kowarik et al., "The cerebrospinal fluid immunoglobulin transcriptome and proteome in neuromyelitis optica reveals central nervous system-specific B cell populations," J Neuroinflammation., 12:19, Jan. 28, 2015.
Kragten et al., "Site-specific analysis of the N-glycans on murine polymeric immunoglobulin A using liquid chromatography/electrospray mass spectrometry," Journal of Mass Spectrometry, 30(12):1679-86, Dec. 1995.
Kroon et al., "Identification of sites of degradation in a therapeutic monoclonal antibody by peptide mapping," Pharmaceutical Research., 9:1386-1393, 1992.
Kyle et al., "Criteria for the classification of monoclonal gammopathies, multiple myeloma and related disorders: a report of the International Myeloma Working Group," Br. J. Haematol., 121(5):749-757, Jun. 2003.
Ladwig et al., "Quantification of serum IgG subclasses by use of subclass-specific tryptic peptides and liquid chromatography-tandem mass spectrometry," Clin Chem., 60(8):1080-1088, May 5, 2014.
Landgren et al., "Monoclonal gammopathy of undetermined significance (MGUS) consistently precedes multiple myeloma: a prospective study" Blood, 113(22):5412-5417, May 28, 2009.
Lavatelli et al., "A novel approach for the purification and proteomic analysis of pathogenic immunoglobulin free light chains from serum," Biochimica et Biophysica Acta., 1814(3):409-419, Mar. 2011.
Lebeau et al., "Generalized crystal-storing histiocytosis associated with monoclonal gammopathy: molecular analysis of a disorder with rapid clinical course and review of the literature," Blood., 100:1817-1827, 2002.
Lefranc, "IMGT, the International ImMunoGeneTics Information System," Cold Spring Harb Protoc., 2011(6):595-603, Jun. 1, 2011.
Legros et al., "Characterization of an anti-Borrelia burgdorferi OspA conformational epitope by limited proteolysis of monoclonal antibody-bound antigen and mass spectrometric peptide mapping," Protein Science, 9(5):1002-10, May 2000.
Leung et al., "A novel and rapid approach to protein expression profiling of cerebrospinal fluid (CSF) from medulloblastoma patients using functionalized magnetic beads, AnchorChipTM technology, MALDI-TOF and MALDI-TOF/TOF mass spectrometry," 33rd Meeting of the Society of Neuroscience, 751.3, Nov. 2003.
Leung et al., "Monoclonal gammopathy of renal significance: when MGUS is no longer undetermined or insignificant," Blood, 120:4292-4295, 2012.
Li et al., "General LC-MS/MS method approach to quantify therapeutic monoclonal antibodies using a common whole antibody internal standard with application to preclinical studies," Analytical Chemistry, 84:1267-1273, 2012.
Li et al., "Simultaneous analysis of multiple monoclonal antibody biotherapeutics by LC-MS/MS method in rat plasma following cassette-dosing," AAPS J., 15(2):337-346, Epub Dec. 12, 2012.
Lindop et al., "Molecular signature of a public clonotypic autoantibody in primary Sjogren's syndrome: A "forbidden" clone in systemic autoimmunity," Arthritis & Rheumatism., 63(11):3477-3486, Oct. 28, 2011.
Liu et al., "Quantitation of a recombinant monoclonal antibody in monkey serum by liquid chromatography-mass spectrometry," Anal Biochem., 414(1):147-153, Epub Mar. 8, 2011.
Lu et al., "Detection of abundant proteins in multiple myeloma cells by proteomics," J Proteomics Bioinform., 3(1):005-009, 2010.
Lu et al., "LC-MS Analysis of Polyclonal Human Anti-Neu5Gc Xeno-Autoantibodies Immunoglobulin G Subclass and Partial Sequence Using Multistep Intravenous Immunoglobulin Affinity Purification and Multienzymatic Digestion," Analytical Chemistry., 84(6):2761-2768, Mar. 20, 2012.
Marien et al., "Detection of monoclonal proteins in sera by capillary zone electrophoresis and free light chain measurements," Clin. Chem., 48(9):1600-1601, Sep. 2002.

(56) References Cited

OTHER PUBLICATIONS

Mazur et al., "A platform for characterizing therapeutic monoclonal antibody breakdown products by 2D chromatography and top-down mass spectrometry," The AAPS journal, 14(3):530-41, Sep. 2012.
McBride et al., "Chromosomal location of human kappa and lambda immunoglobulin light chain constant region genes," J Exp Med., 155(5):1480-1490, May 1, 1982.
Merlini and Palladini, "Differential diagnosis of monoclonal gammopathy of undetermined significance" Hematology, 595-603, 2012.
Micallef, J. et al, Journal of Hematology & Oncology 2010, 3, 11 pages.
Mills et al., "Using mass spectrometry to quantify rituximab and perform individualized immunoglobulin phenotyping in ANCA-associated vasculitis," Analytical chemistry, 88(12):6317-25, Jun. 2016.
Minnura et al., "Contrasting glycosylation profiles between Fab and Fc of a human IgG protein studied by electrospray ionization mass spectrometry," J. Immunol. Methods., 326(1-2):116-26, Sep. 2007.
Mohr et al., "High-efficiency nano- and micro-HPLC—high-resolution Orbitrap—MS platform for top-down proteomics," Proteomics., 10(20):3598-3609, Oct. 2010.
Mukhopadhyay et al., "A tribute to Frank Anscombe and random central limit theorem from 1952," Sequential Analysis, 31(3): 265-277, 2012.
Murphy et al., "Characterization of systemic amyloid deposits by mass spectrometry," Methods Enzymol., 412:48-62, 2006.
Murray et al., "Characterization of immunoglobulin by mass spectrometry with applications for the clinical laboratory," Crit. Rev. Clin Lab. Sci., 50(4-5):91-102, Jul.-Oct. 2013.
Nasr et al., "Immunotactoid glomerulopathy: clinicopathologic and proteomic study," Nephrol Dial Transplant., 27(11):4137-4146, Epub Aug. 7, 2012.
Obermeier et al., "Matching of oligoclonal immunoglobulin transcriptomes and proteomes of cerebrospinal fluid in multiple sclerosis," Nat Med., 14(6):688-693, Epub May 18, 2008.
Oeckl et al., "CSF concentrations of cAMP and cGMP are lower in patients with Creutzfeldt-Jakob disease but not Parkinson's disease and amyotrophic lateral sclerosis," PLoS One, 7(3):e32664, Mar. 2012.
Pang et al., "Biomarker discovery in urine by proteomics," Journal of Proteome Research, 1:161-169, Epub Feb. 16, 2002.
Piehler et al., "Quantitation of serum free light chains in combination with protein electrophoresis and clinical information for diagnosing multiple myeloma in a general hospital population," Clin. Chem., 54(11):1823-1830, Nov. 2008.
Qin et al., "Development of a "reverse capture" autoantibody microarray for studies of antigen-autoantibody profiling," Proteomics., 6(10):3199-209, May 2006.
Radovic, V. V.,"Recommendations for Use of Free Light Chain Assay in Monoclonal Gammopathies" Journal of Medical Biochemistry, 29:1-8, 2010.
Rajkumar et al., "Advances in the diagnosis, classification, risk stratification, and management of monoclonal gammopathy of undetermined significance: implications for recategorizing disease entities in the presence of evolving scientific evidence," Mayo Clinic Proceedings., 85:945-948, 2010.
Reid et al., "Rapid whole monoclonal antibody analysis by mass spectrometry: An ultra scale-down study of the effect of harvesting by centrifugation on the post-translational modification profile," Biotechnology and Bioengineering, 107(1):85-95, Sep. 2010.
Remily-Wood et al., "A database of reaction monitoring mass spectrometry assays for elucidating therapeutic response in cancer," Proteomics Clinical Applications, 5:383-396, 2011.
Ren et al., "Reversed-phase liquid chromatography-mass spectrometry of site-specific chemical modifications in intact immunoglobulin molecules and their fragments," J Chromatography A., 1179:198-204, 2008.

Rodriguez et al., "Immunoglobulin derived depositions in the nervous system: novel mass spectrometry application for protein characterization in formalin-fixed tissues," Lab Invest., 88(10):1024-1037, Epub Aug. 18, 2008.
Rosati et al., "Exploring an orbitrap analyzer for the characterization of intact antibodies by native mass spectrometry," Angew. Chem. Int. Ed. Engl., 51(52):12992-12996, Dec. 2012.
Ruan et al., "Strategy and its implications of protein bioanalysis utilizing high-resolution mass spectrometric detection of intact protein," Anal. Chem., 83(23):8937-8944, Dec. 2011.
Schaefer et al., "Residual serum monoclonal protein predicts progression-free survival in patients with previously untreated multiple myeloma," Cancer., 116:640-646, 2010.
Sethi et al., "Mass spectrometry-based proteomic diagnosis of renal immunoglobulin heavy chain amyloidosis," Clin J Am Soc Nephrol., 5:2180-2187, 2010.
Singh et al., "Cerebrospinal-fluid-derived immunoglobulin G of different multiple sclerosis patients shares mutated sequences in complementarity determining regions," Mol Cell Proteomics, 12(12):3924-3934, Epub Aug. 22, 2013.
Song et al., "Characterization of N-terminal processing of group via phospholipase A2 and of potential cleavage sites of amyloid precursor protein constructs by automated identification of signature peptides in LC/MS/MS analyses of proteolytic digests," J Am Soc Mass Spectrom., 15(12):1780-1793, Dec. 2004.
Stoop et al., "Quantitative MALDI-FT-ICR analysis of cerebrospinal fluid of relapsing-remitting and primary progressive multiple sclerosis patients," Multiple Sclerosis., 15(9):S83, Sep. 2009.
Stubbs et al., "Anti-neurofilament antibodies in neuropathy with monoclonal gammopathy of undetermined significance produce experimental motor nerve conduction block," Acta Neuropathology., 105:109-116, 2003.
Sun et al., "Immunoglobulin genes and diversity: what we have learned from domestic animals," J Anim Sci Biotechnol., 3(1):18, Jun. 20, 2012.
Sun et al., "Preparation and mass spectrometric study of egg yolk antibody (IgY) against rabies virus," Rapid communications in mass spectrometry, 15(9):708-12, May 2001.
Theis et al., "Immunoglobulin Light Chain Gene Constant Region Is an Invariable Part of Amyloid Deposits in AL Amyloidosis," Blood, 112(11):3128, Nov. 16, 2008.
Theis et al., "Mass spectrometry based proteomic analysis of AL amyloidosis: Immunoglobulin Light Chain Gene Constant Region Is an Invariable Part of Amyloid Deposits and provides valuable diagnostic target," presented at The United States and Canadian Academy of Pathology Annual Meeting, Mar. 2009, 1 page.
Thermo Scientific, "MelonTM Gel IgG Spin Purification Kit" [online], 2011 [retrieved on Aug. 6, 2015]. Retrieved from the Internet: <URL: https://tools.lifetechnologies.com/content/sfs/manuals/MAN0011513_Melon_Gel_1gG_Spin_Purifi_UG.pdf, 4 pages.
Thurgood et al., "An Immunodominant La/SSB autoantibody proteome derives from public clonotypes," Clinical and Experimental Immunology., 174:237-244, Oct. 6, 2013.
VanDuijn et al., "Immune responses are characterized by specific shared immunoglobulin peptides that can be detected by proteomic techniques," Journal of Biological Chemistry, 285:29247-29253, Jul. 8, 2010.
Verheesen et al., "Beneficial properties of single-domain antibody fragments for application in immunoaffinity purification and immunoperfusion chromatography," Biochim Biophys Acta., 1624(1-3):21-28, Dec. 5, 2003.
Vrana et al., "Classification of amyloidosis by laser microdissection and mass spectrometry-based proteomic analysis in clinical biopsy specimens," Blood, 114(24):4957-4960, Dec. 2009.
Vrana et al., "Amyloidosis typing based on Laser Microdissection and Mass Spectrometry of Paraffin-Embedded Tissue Biopsies" Companion to Peripheral Neuropathy, pp. 347-349, 2010.
Vrana et al., "Classification of Amyloidosis in Fat Aspiration Specimens Using Mass Spectrometry Based Proteomics," presented at The United States and Canadian Academy of Pathology Annual Meeting, Mar. 2009, 1 page.

(56) References Cited

OTHER PUBLICATIONS

Vrana et al., "Diagnosis and Classification of Amyloidosis in Abdominal Subcutaneous Fat Aspiration Specimens Using Mass Spectrometry Based Proteomics," Blood, 112(11):2710, Nov. 16, 2008.
Vrana et al., "Diagnosis and Typing of Cardiac Amyloidosis in Routine Clinical Specimens by Mass Spectrometry Based Proteomic Analysis," presented at The United States and Canadian Academy of Pathology Annual Meeting, Mar. 2009, 1 page.
Wagner-Rousset et al., "The way forward, enhanced characterization of therapeutic antibody glycosylation: comparison of three level mass spectrometry-based strategies," Journal of Chromatography B, 872(1-2):23-37, Sep. 2008.
Wang et al., "Construction of a Multiple Myeloma Diagnostic Model by Magnetic Bead-Based MALDI-TOF Mass Spectrometry of Serum and Pattern Recognition Software" Anatomical Record, 292:604-610, 2009.
Wang et al., "Differentiation and quantification of endogenous and recombinant-methionyl human leptin in clinical plasma samples by immunocapture/mass spectrometry," J. Pharm. Biomed. Anal., 70:440-446, Nov. 2012.
Wang et al., "Molecular basis of assembly and activation of complement component C1 in complex with immunoglobulin G1 and antigen," Molecular cell, 63(1):135-45, Jul. 2016.
Whiteaker et al., "Sequential multiplexed analyte quantification using peptide immunoaffinity enrichment coupled to mass spectrometry," Mol Cell Proteomics., 11(6):10.1074/mcp.M111.015347, 2012,10 pages.
Willrich et al., "Quantitation of infliximab using clonotypic peptides and selective reaction monitoring by LC-MS/MS," International Immunopharmacology., 28(1): 513-520, Sep. 1, 2015.
Willrich et al., "Serum infliximab quantitation by LC-MS/MS in patients treated for inflammatory disorders," Gastroenterology AGA Abstracts., Sa1252, May 1, 2014, Retrieved from the internet: URL:https://ac.els-cdn.com/SOO16508514608568/1-S2.0-S0016508514608568-mai n.pdf?_ti d=e58e3b4c-caOa-lle7-96b2-OOOO0aabOf6b&acdnat=1510753563_74ab7a6bOb5f976b8c948a995d894fce, Retrieved on Nov. 15, 2017, Abstract Only.
Wine, Y. et al. Molecular deconvolution of the monoclonal antibodies that comprise the polyclonal serum response, PNAS vol. 110, No. 8, pp. 2993-2998 (Year: 2013).
Written Opinion of the International Searching Authority in International Application No. PCT/US2017/050430 dated Nov. 27, 2017, 16 pages.
Yamazaki et al., "A proteolytic modification of AIM promotes its renal excretion," Scientific Reports, 6:38762, Dec. 2016.
Zhang et al., "Characterization of variable regions of monoclonal antibodies by top-down mass spectrometry," Anal Chem., 79(15):5723-5729, 2007.
Zhaoyu et al., "Alteration of DBP levels in CSF of patients with MS by proteomics analysis," Cell Mol. Neurobiol., 29(2):203-210, Mar. 2009.
Acera et al., "Changes in tear protein profile in keratoconus disease," Eye, 25(9):1225-33, Sep. 2011.
Attealnnannan and Levinson et al., "Understanding and Identifying monoclonal gammopathies," Clinical Chemistry, Aug. 2000, 46(8B):1230-1238.
Balakrishnan et al., "Differential proteomic analysis of synovial fluid from rheumatoid arthritis and osteoarthritis patients," Clin. Proteomics., 11(1):1, 2014.
Baldini et al., "Correspondence between salivary proteomic pattern and clinical course in primary Sjögren syndrome and non-Hodgkin's lymphoma: a case report," Journal of translational medicine, 9(1):188, Dec. 2011.
Chow et al., "Serum immune-related proteins are differentially expressed during hibernation in the American black bear," PLoS One, 8(6), 2013.

Cohen et al., "β-Elimination and peptide bond hydrolysis: two distinct mechanisms of human IgG1 hinge fragmentation upon storage," Journal of the American Chemical Society, 129(22):6976-7, Jun. 2007.
Cretu, "Identification and Validation of Candidate Soluble Biomarkers for Psoriatic Arthritis Using Quantitative Proteomics (Doctoral dissertation)", 2015.
Dai Y, Hu C, Huang Y, Huang HY, Liu J, Lv T. A proteomic study of peripheral blood mononuclear cells in systemic lupus erythematosus. Lupus. Sep. 2008;17(9):799-804.
Deng et al., "Plasma proteomic analysis of pancreatic cancer by 2-dimensional gel electrophoresis," Pancreas, 34(3):310-7, Apr. 2007.
Deshpande et al., "GlycoSpectrumScan: fishing glycopeptides from MS spectra of protease digests of human colostrum sIgA," Journal of proteome research, 9(2):1063-75, Feb. 2010.
Ellias et al., "Proteomic analysis of saliva identifies potential biomarkers for orthodontic tooth movement," The Scientific World Journal, 2012.
Ghafouri et al., "Newly identified proteins in human nasal lavage fluid from non-smokers and smokers using two-dimensional gel electrophoresis and peptide mass fingerprinting," Proteomics: International Edition, 2(1):112-20, Jan. 2002.
Goetze et al., "High-mannose glycans on the Fc region of therapeutic IgG antibodies increase serum clearance in humans," Glycobiology, 21(7):949-59, Jul. 2011.
Grazio et al., "Differential expression of proteins with heparin affinity in patients with rheumatoid and psoriatic arthritis: a preliminary study," Clin. Exp. Rheumatol., 31(5):665-671, 2013.
Huang et al., "Site-specific glycosylation of secretory immunoglobulin A from human colostrum. Journal of proteome research," 14(3):1335-49, Mar. 2015.
Hutchison et al., "The pathogenesis and diagnosis of acute kidney injury in multiple myeloma," Nature Reviews Nephrology, Jan. 2012, 8:43-51.
Iannaccone et al., "Retinal pigment epithelium and microglia express the CD5 antigen-like protein, a novel autoantigen in age-related macular degeneration," Exp Eye Res., 155:64-74, 2017.
Kim et al., "Prediction of Response to Sorafenib in Hepatocellular Carcinoma: A Putative Marker Panel by Multiple Reaction Monitoring-Mass Spectrometry (MRM-MS)," Mol. Cell Proteomics., 16(7):1312-132, 2017.
Kiselar et al., "Direct Identification of Protein Epitopes by Mass Spectrometry Without Immobilization of Antibody and Isolation of Antibody-Peptide Complexes," Analytical Chemistry, May 1999, 71(9):1792-1801.
Kissel and Mendell, "Neuropathies associated with monoclonal gammopathies," Neuromuscular disorders, Jan. 1996, 6(1):3-18.
Koh et al., "Characterization of exosomes from body fluids of dairy cows," J. Anim. Sci., 95(9):3893-3904, 2017.
Kolialexi et al., "Plasma biomarkers for the identification of women at risk for early-onset preeclampsia," Expert Rev. Proteomics., 14(3):269-276, 2017.
Kurokawa et al., "Macrophage-derived AIM is endocytosed into adipocytes and decreases lipid droplets via inhibition of fatty acid synthase activity," Cell metabolism, 11(6):479-92, Jun. 2010.
Lee et al., "Relationship between Group-Specific Component Protein and the Development of Asthma," American journal of respiratory and critical care medicine 184(5):528-536, 2011.
Lill et al., "Microwave-assisted proteomics," Mass spectrometry reviews, 26(5):657-71, Sep. 2007.
Lim et al., "Identification and Location of a Cysteinyl Post-translational Modification in an Amyloidogenic kappa 1 Light Chain Protein by Electrospray Ionization and Matrix-Assisted Laser Desorption/Ionization Mass Spectrometry," Analytical Biochemistry, Aug. 2001, 295:45-56.
Liu et al., "Analysis of plasma proteome from cases of the different traditional Chinese medicine syndromes in patients with chronic hepatitis B," Journal of Pharmaceutical and Biomedical Analysis, 59:173-178, 2012.
Lokamani et al., "Gelsolin and ceruloplasmin as potential predictive biomarkers for cervical cancer by 2D-DIGE proteomics analysis," Pathology & Oncology Research, 20(1):119-29, Jan. 2014.

(56) References Cited

OTHER PUBLICATIONS

Markowitz, "Dysproteinemia and the Kidney," Advances in Anatomic Pathology, Jan. 2004, 11:49-63.
Mischak et al., "Urinary proteome analysis using capillary electrophoresis coupled to mass spectrometry: a powerful tool in clinical diagnosis, prognosis and therapy evaluation," Journal of Medical Biochemistry, Oct. 2009, 28(4):223-234.
Mitchell et al., "Alterations in the bovine bronchoalveolar lavage proteome induced by dexamethasone," Veterinary immunology and immunopathology, 118(3-4):283-93, Aug. 2007.
Moh et al., "Site-specific N-glycosylation of recombinant pentameric and hexameric human IgM," Journal of the American Society for Mass Spectrometry, 27(7):1143-55, Apr. 2016.
Okamoto et al., "Proteome analysis of bronchoalveolar lavage fluid in chronic hypersensitivity pneumonitis," Allergology International, 61(1):83-92, Jan. 2012.
Oruc et al., "IgA structure variations associate with immune stimulations and IgA mesangial deposition," Journal of the American Society of Nephrology, 27(9):2748-61, Sep. 2016.
Pabst et al., "A microarray-matrix-assisted laser desorption/ionization-mass spectrometry approach for site-specific protein N-glycosylation analysis, as demonstrated for human serum immunoglobulin M (IgM)," Molecular & Cellular Proteomics, 14(6):1645-56, Jun. 2015.
Persson et al., "Development of Mass Spectrometry Based Techniques for the Identification and Determination of Compositional Variability in Recombinant Polyclonal Antibody Products," Analytical Chemistry, Sep. 2010, 82(17):7274-7282.
Roberts et al., "An Integrated Strategy for Structural Characterization of the Protein and Carbohydrate Components of Monoclonal Antibodies: Application to Anti-Respiratory Syncytial Virus Mab," Analytical Chemistry, Oct. 1995, 67(20):3613-3625.
Salinas et al., "Buffer-dependent fragmentation of a humanized full-length monoclonal antibody," Journal of pharmaceutical sciences, 99(7):2962-74, Jul. 2010.
Sandoval et al., "Rapid removal of N-linked oligosaccharides using microwave assisted enzyme catalyzed deglycosylation," International Journal of Mass Spectrometry, 259(1-3):117-23, Jan. 2007.
Sanjurjo et al., "AIM/CD5L: a key protein in the control of immune homeostasis and inflammatory disease," J. Leukoc. Biol., 98(2):173-184, Aug. 2015.
Sarrias et al., "Biochemical characterization of recombinant and circulating human Spα," Tissue antigens, Apr. 2004, 63(4):335-44.
Shaheen et al., "Multiple Myeloma and Immunosecretory Disorders: An Update," Advances in Anatomic Pathology, Jul. 2008, 15(4):196-210.
Sikkink et al., "Biochemical and Aggregation Analysis of Bence Jones Proteins From Different Light Chain Diseases," Amyloid, Mar. 2008, 15:29-39.
Skriner et al., "Association of citrullinated proteins with synovial exosomes," Arthritis & Rheumatism: Official Journal of the American College of Rheumatology, Dec. 2006, 54(12):3809-14.
Tissot et al., "IgM Are Associated to Sp Alpha (CD5 Antigen-Like)," Electrophoresis, 23(7-8):1203-1206, Apr. 2002.
Vase et al., "A57 Proteomic profiling of pretreatment serum from HIV-infected patients identifies candidate markers predictive of lymphoma development," AIDS, 2016, 30(12):1889-1898.
Vlasak and Ionescu, "Fragmentation of monoclonal antibodies," mAbs, 3:253-263, May 2011.
Wang et al., "Discovery of potential colorectal cancer serum biomarkers through quantitative proteomics on the colonic tissue interstitial fluids from the AOM-DSS mouse model," J. Proteomics, 2016, 132:31-40.
Wang et al., "Structural Characterization of a Recombinant Monoclonal Antibody by Electrospray Time-of-Flight Mass Spectrometry," Pharmaceutical Research, Aug. 2005, 22(8):1338-1349.
Xu et al., "Discovery and identification of serum potential biomarkers for pulmonary tuberculosis using iTRAQ-coupled two-dimensional LC-MS/MS," Proteomics, 2014, 14(2-3):322-331.
Yin et al., "Protein biomarkers of new-onset cardiovascular disease: prospective study from the systems approach to biomarker research in cardiovascular disease initiative," Arterioscler. Thromb. Vasc. Biol., 2014, 34(4):939-945.
Zhang et al., "Proteomic analysis of plasma in adult active pulmonary tuberculosis patients with diabetes mellitus," The FASEB Journal, Apr. 2015, 29(1_supplement):275-7.
Zhong et al., "Microwave-assisted acid hydrolysis of proteins combined with liquid chromatography MALDI MS/MS for protein identification," Journal of the American Society for Mass Spectrometry, Apr. 2005, 16(4):471-81.
Zhong et al., "Protein sequencing by mass analysis of polypeptide ladders after controlled protein hydrolysis," Nature biotechnology, Oct. 2004, 22(10):1291-6.
Zhou et al., "Quantitative analysis of N-linked glycoproteins in tear fluid of climatic droplet keratopathy by glycopeptide capture and iTRAQ," Journal of proteome research, Apr. 2009, 8(4):1992-2003.
Extended European Search Report in European Application No. 17849511.5 dated Apr. 24, 2020, 12 pages.
Fan et al., "A single proteolytic cleavage within the lower hinge of trastuzumab reduces immune effector function and in vivo efficacy," Breast Cancer Research, Aug. 2012, 14(4):R116.
Hess et al., "Immunoglobulin cleavage by the streptococcal cysteine protease IdeS can be detected using protein G capture and mass spectrometry," Journal of microbiological methods, Aug. 2007, 70(2):284-91.
Ito and Arata, "Proton nuclear magnetic resonance study on the dynamics of the conformation of the hinge segment of human G1 immunoglobulin," Biochemistry, Nov. 1985, 24(23):6467-74.
Sloane et al., "Proteomic analysis of sputum from adults and children with cystic fibrosis and from control subjects. American journal of respiratory and critical care medicine," Dec. 2005, 172(11):1416-26.
Botz et al., "Detecting monoclonal light chains in urine: micro LC-ESI-Q-TOF mass spectrometry compared to immunofixation electrophoresis," British journal of haematology, 167(3):437-8, Nov. 2014.

* cited by examiner

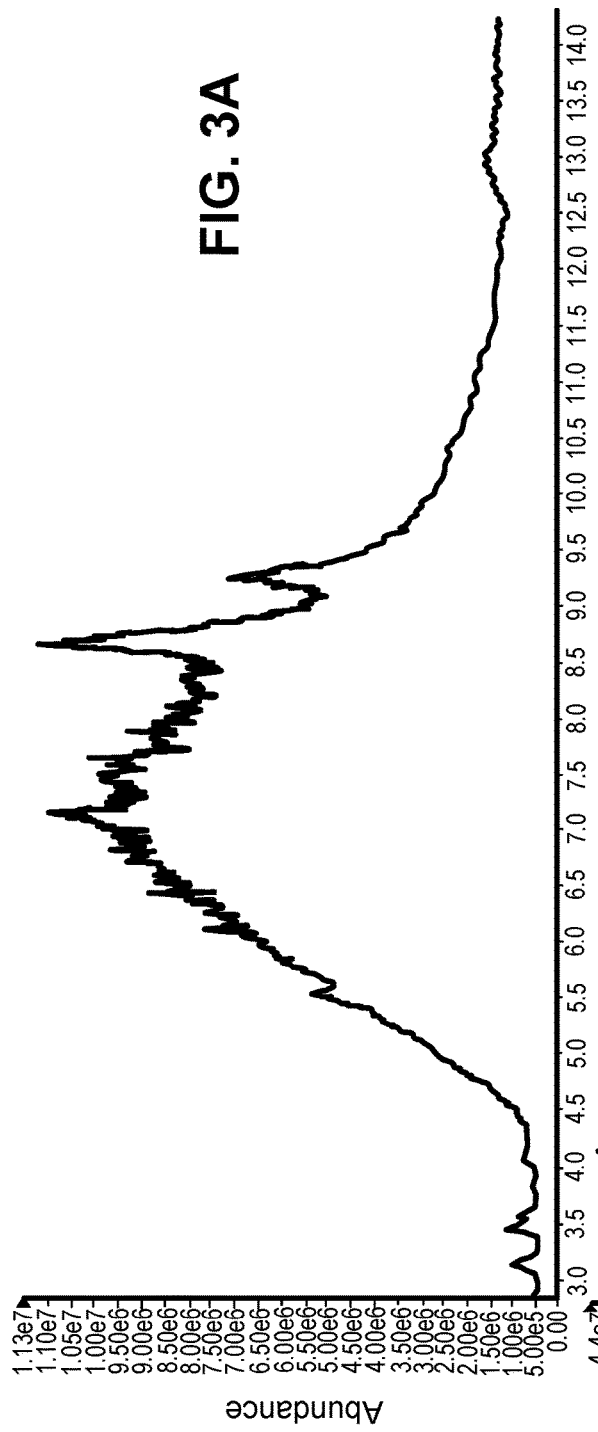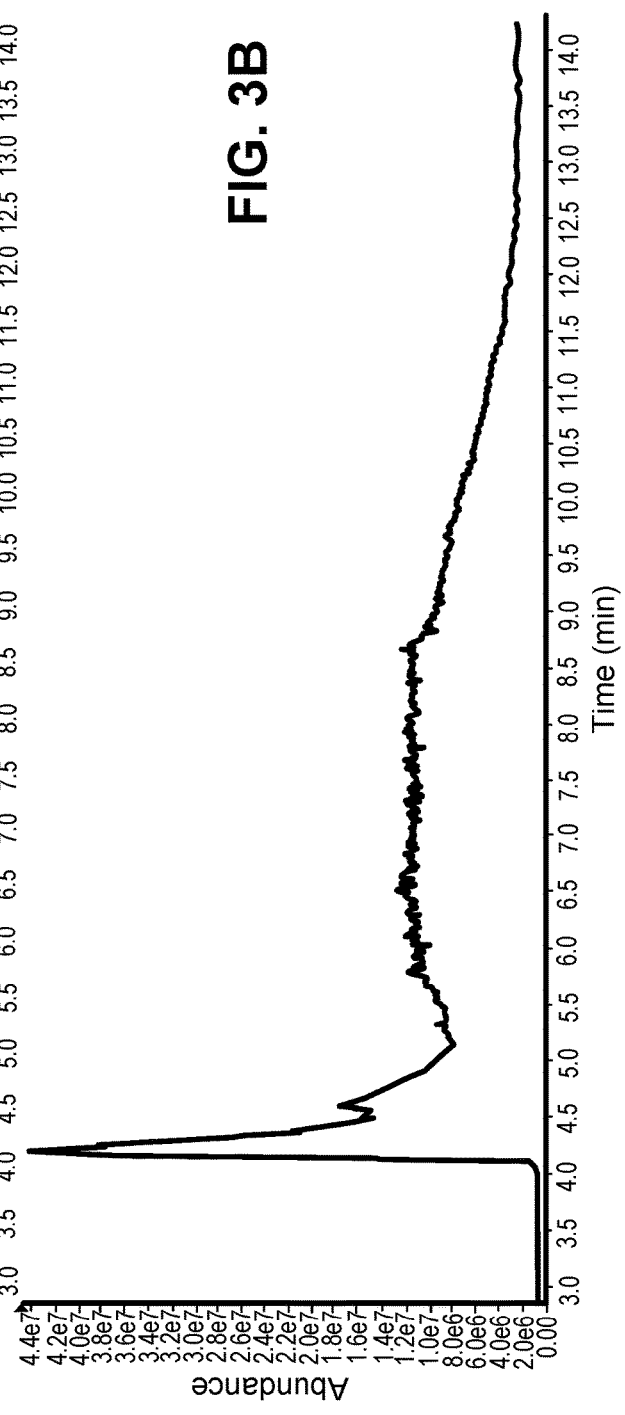

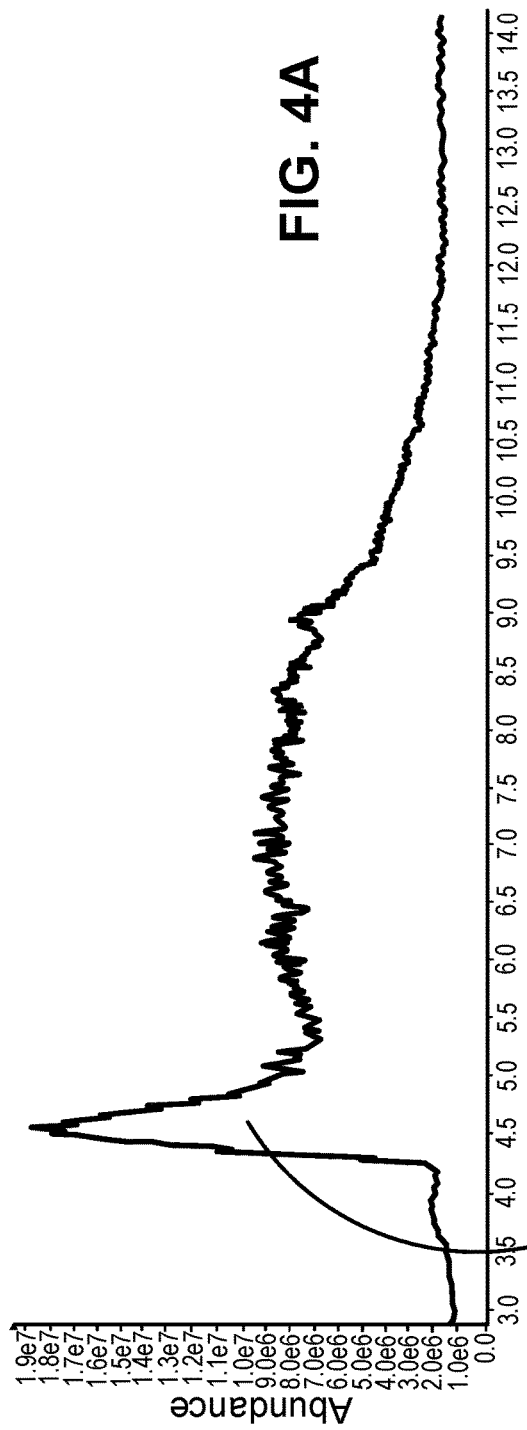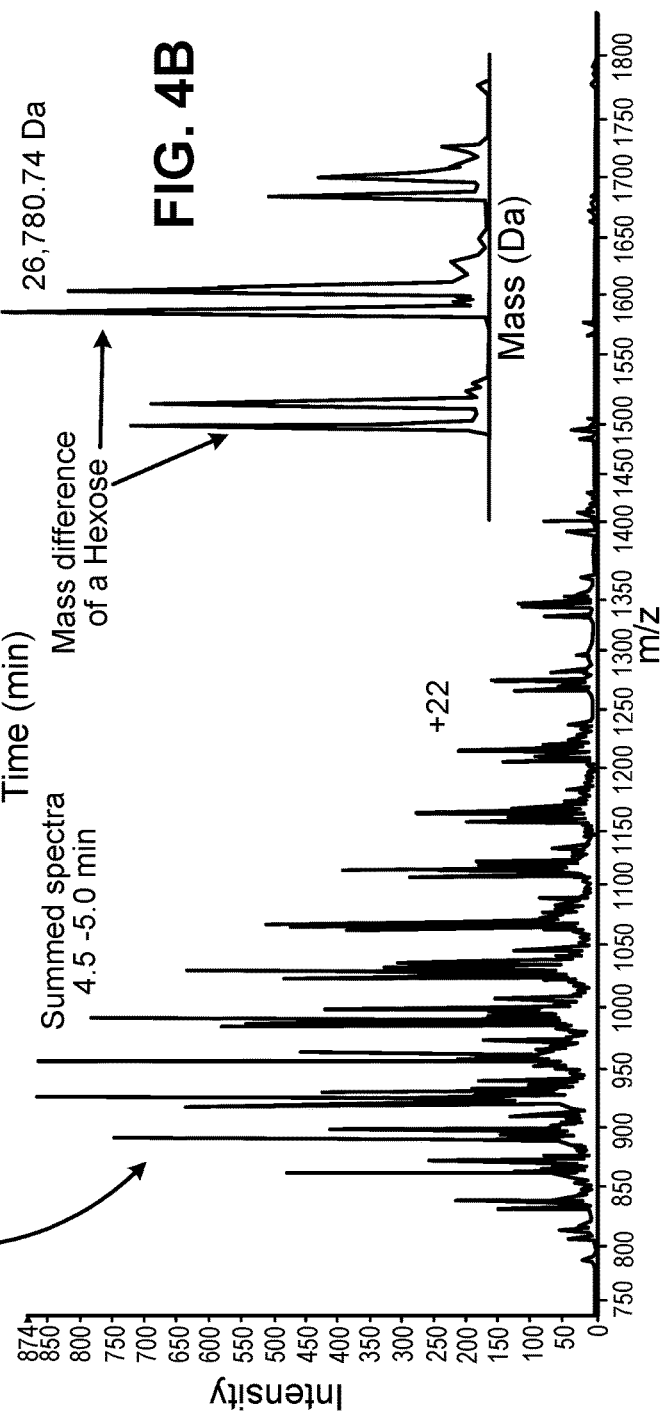

IDENTIFICATION AND MONITORING OF CLEAVED IMMUNOGLOBULINS BY MOLECULAR MASS

CROSS-REFERENCE TO RELATED APPLICATIONS

This application is a National Stage application under 35 U.S.C. § 371 of International Application No. PCT/US2017/050430, having an International Filing Date of Sep. 7, 2017, which claims priority to U.S. Application Ser. No. 62/384,445, filed on Sep. 7, 2016. The disclosures of the prior applications are considered part of the disclosure of this application, and are incorporated in their entirety into this application.

BACKGROUND

1. Technical Field

This document relates to materials and methods for identifying and monitoring immunoglobulin cleavage (e.g., IgG cleavage) in a sample, such as a biological sample, using mass spectrometry techniques.

2. Background Information

Immunoglobulins of the IgG isotype can be cleaved by exogenous enzymes such as papain and the IgG-degrading enzyme of *Streptococcus pyogenes* (IdeS). These enzymes generate fragments referred to as the Fc portion (which contains the constant region of the heavy chain) and the Fab' or F(ab')2 portion (which contains the variable region of the heavy chain along with the light chain). These IgG fragments have typically been monitored in serum using low resolution gel electrophoresis.

SUMMARY

This document provides materials and methods for identifying and monitoring immunoglobulin cleavage (e.g., IgG cleavage) in a sample, such as a biological sample, using mass spectrometry techniques.

As demonstrated herein, there are endogenous enzymes (e.g., plasmin) that can cleave IgG in vivo creating IgG cleavage products. The accurate molecular mass of Fc and Fab fragments coupled with top-down MS can be used to identify cleavage of IgG by plasmin in patient serum suggesting activation of the complement system. This methodology holds promise as a sensitive and specific diagnostic tool to aid in monitoring a patient's immune system.

In general, one aspect of this document features a method for detecting IgG cleavage in a patient, a method for identifying plasmin activation in a patient, and a method for detecting complement activation in a patient. The methods include, or consists essentially of, providing a sample comprising IgG from the patient, subjecting the sample to a mass spectrometry technique to obtain a mass spectrum of the sample, and identifying the presence of an IgG cleavage fragment. The sample can be suspected to have plasmin IgG cleavage. The sample can be a blood sample (e.g., a serum sample). The patient can be a human. The IgG cleavage fragment can be a plasmin generated IgG cleavage fragment. The IgG cleavage fragment can include the amino acid sequence THTCPPCPAPEL (SEQ ID NO:2). The IgG cleavage fragment can be glycosylated. The IgG cleavage fragment can be from a polyclonal IgG or from a monoclonal IgG. A method described herein can also include isolating the IgG from the sample. A method described herein can also include enriching the IgG from the sample. A method described herein can also include contacting the sample with a reducing agent prior to subjecting the sample to the mass spectrometry technique. The reducing agent can be dithiothreitol (DTT). The mass spectrometry technique can be electrospray ionization mass spectrometry (ESI-MS). The ESI-MS technique can include a quadrupole time-of-flight (TOF) mass spectrometer. The mass spectrometry technique can be a top-down mass spectrometry technique.

In another aspect, this document features a method for identifying an inflammatory condition in a patient. The method includes, or consists essentially of, providing a sample from the patient, subjecting the sample to a mass spectrometry technique to obtain a mass spectrum of the sample, and identifying the presence of an IgG cleavage fragment. The sample can be a blood sample (e.g., a serum sample). The patient can be a human. The IgG cleavage fragment can include an Fc fragment. The Fc fragment can be glycosylated. The IgG can be a polyclonal IgG or a monoclonal IgG. The method can also include isolating the IgG from the sample. The methods can also include contacting the sample with a reducing agent prior to subjecting the sample to the mass spectrometry technique. The reducing agent can be DTT. The mass spectrometry technique can be ESI-MS. The ESI-MS technique can include a quadrupole TOF mass spectrometer. The mass spectrometry technique can be a top-down mass spectrometry technique. The method can include distinguishing an autoimmune inflammatory condition from an infectious inflammatory condition in the subject. A sample from a patient having the autoimmune inflammatory condition can include a plasmin generated IgG cleavage fragment. The plasmin generated IgG cleavage fragment can include the amino acid sequence THTCPPCPAPEL (SEQ ID NO:2). The autoimmune inflammatory condition can be Sjögren's syndrome, rheumatoid arthritis, lupus erythematosus, or vasculitis. A sample from a patient having the infectious inflammatory condition can include an IgG-degrading enzyme of *Streptococcus pyogenes* (IdeS) generated IgG cleavage fragment. The infection can be a *Streptococcus pyogenes* infection.

In another aspect, this document features a method for monitoring plasmin activation in a subject and a method for monitoring a treatment of an immune disease in a patient. These methods include, or consists essentially of, providing a first sample of the patient obtained before the treatment and a second sample of the patient obtained during or after the treatment, subjecting the first and second samples to a mass spectrometry technique to obtain a mass spectrum of the first and second samples, determining the amount of IgG cleavage fragment in the first and second samples, and comparing the amount of the IgG cleavage fragment in the first and second samples. The methods can include isolating the IgG from the first sample and isolating the IgG from the second sample. The methods can include contacting the first sample and the second sample with a reducing agent prior to subjecting the first sample and the second sample to the mass spectrometry technique. The reducing agent can be DTT. The mass spectrometry technique can be ESI-MS. The ESI-MS technique can include a quadrupole TOF mass spectrometer. The mass spectrometry technique can be a top-down mass spectrometry technique. The immune disease can be an autoimmune disease (e.g., Sjögren's syndrome, rheumatoid arthritis, lupus erythematosus, or vasculitis). A sample from a patient having the autoimmune inflammatory condition can include a plasmin generated IgG cleavage fragment. The plasmin generated IgG cleavage fragment can include the amino acid sequence THTCPPCPAPEL (SEQ ID NO:2). In some cases, determining the amount of IgG cleavage fragment in the first and second samples can include determining the concentration of IgG cleavage fragment in the first and second samples, and the comparing the amount of the IgG cleavage fragment in the first and second samples can include comparing the concentration of the IgG cleavage fragment in the first and second samples.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4 contains MS analyses of plasmin cleaved serum. A) A TIC from a patient with suspected plasmin immunoglobulin cleavage activity. B) A summed mass spectra and a deconvoluted mass spectrum (inset).

DETAILED DESCRIPTION

This document provides materials and methods for identifying and monitoring immunoglobulin cleavage in a sample using mass spectrometry techniques. For example, the materials and methods provided herein can be used to identify and monitor IgG cleavage. The use of mass over charge (m/z), optionally with additional techniques, such as gel electrophoresis and/or peptide sequencing, provides a more direct assessment of the IgG cleavage fragment because it can identify plasmin activation in a sample from a patient and/or detect complement activation in a patient. These methods are useful for screening biological samples for the presence or absence of an IgG cleavage fragment, for identifying an inflammatory condition in a patient, for monitoring plasmin activation in a patient, and/or for monitoring treatment of an immune disease in a patient.

Figure 1:
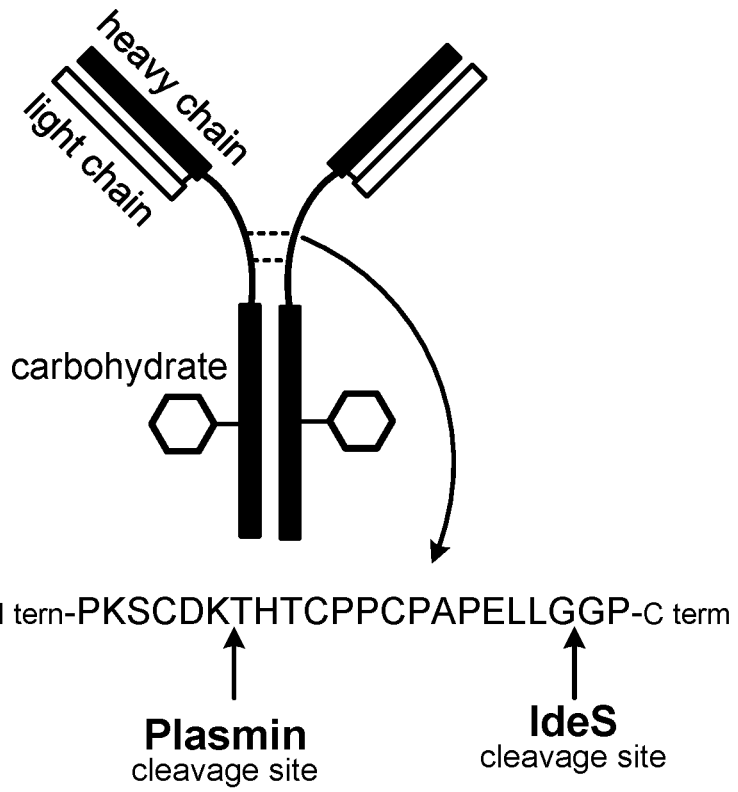
FIG. 1 is a schematic model of an IgG immunoglobulin with a close up of the heavy chain amino acid sequence (SEQ ID NO:1) in the hinge region where plasmin and IdeS cleave the molecule into Fc and F(ab') or F(ab')2 fragments.

Described herein are enzyme generated IgG cleavage fragments. IgG cleavage fragments can be generated by any appropriate enzyme. In some cases, the enzyme can be an endogenous enzyme. For example, IgG cleavage fragments can be plasmin-generated IgG cleavage fragments. Plasmin cleaves IgG in the heavy chain hinge to generate Fc and F(ab') or F(ab')2 fragments. A portion of the IgG heavy change hinge sequence (SEQ ID NO:1) including the plasmin cleavage site is shown in FIG. 1. A plasmin-generated IgG cleavage fragment can include the amino acid sequence THTCPPCPAPEL (SEQ ID NO:2) at its N-terminus. For example, a plasmin-generated IgG cleavage fragment can include the amino acid sequence THTCPPCPA-PELLGGPSVFLFPPKPKDTLMISRTPE-VTCVVVDVSHEDPEVKFNWY VDGVEVHNAKTKPREEQYN-STYRVVSVLTVLHQDWLNGKEYKCKVSNKALPAP IEKTISKAKGQPREPQVYTLPPSRDELTKNQVSLT-CLVKGFYPSDIAVEWESNGQPE NNYKTTPPVLDSDGSFFLYSK-LTVDKSRWQQGNVFSCSVMHEALHNHYTQKSLS LSPGKGK (SEQ ID NO:3) at its N-terminus. In some cases, a plasmin-generated IgG cleavage fragment can be glycosylated. A glycosylated cleavage fragment can include any appropriate carbohydrate (e.g., hexose or sialic acid).

IgG cleavage fragments described herein (e.g., plasmin-generated IgG fragments) can be detected using mass spectroscopy. The speed, sensitivity, resolution, and robustness of mass spectroscopy make the present methods superior than gel electrophoresis for screening samples for IgG fragments. A method described herein can include the use of a liquid chromatography mass spectrometry (LC-MS). In some cases, electrospray ionization mass spectrometry (ESI-MS) techniques can be used, for example, an electrospray ionization quadrupole time-of-flight mass spectrometry (ESI-Q-TOF MS) technique. In some cases, a mass spectrometry technique can be a top-down mass spectrometry technique.

Samples and Sample Preparation

The materials and methods for identifying and monitoring immunoglobulin cleavage (e.g., IgG cleavage) described herein can include any appropriate sample. A sample can be any biological sample, such as a tissue (e.g., adipose, liver, kidney, heart, muscle, bone, or skin tissue) or biological fluid (e.g., blood, serum, plasma, urine, lachrymal fluid, or saliva). The sample can be from a patient that has immunoglobulins, which includes but is not limited to a mammal, e.g. a human, dog, cat, primate, rodent, pig, sheep, cow, horse, bird, reptile, or fish. A sample can also be a man-made reagent, such as a mixture of known composition or a control sample. In some cases, the sample is serum from a human patient.

A sample can be treated to remove components that could interfere with the mass spectrometry technique. A variety of techniques known to those having skill in the art can be used based on the sample type. Solid and/or tissue samples can be ground and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added. For example, whole blood samples can be treated using conventional clotting techniques to remove red and white blood cells and platelets. A sample can be deproteinized. For example, a plasma sample can have serum proteins precipitated using conventional reagents such as acetonitrile, KOH, NaOH, or others known to those having ordinary skill in the art, optionally followed by centrifugation of the sample.

Immunoglobulins can be isolated from the samples or enriched (i.e. concentrated) in a sample using standard methods known in the art. Such methods include removing one or more non-immunoglobulin contaminants from a sample. In some cases, the samples can be enriched or purified using immunopurification, centrifugation, filtration, ultrafiltration, dialysis, ion exchange chromatography, size exclusion chromatography, protein A/G affinity chromatography, affinity purification, precipitation, gel electrophoresis, capillary electrophoresis, chemical fractionation (e.g., antibody purification kits, such as Melon Gel Purification), and aptamer techniques. For example, the immunoglobulins can be purified by chemical-based fractionation, e.g., Melon Gel Chromatography (Thermo Scientific), where Melon Gel resins bind to non-immunoglobulin proteins in a sample and allow immunoglobulins to be collected in the flow-through fraction; or by affinity purification, e.g., by Protein A, Protein G, or Protein L purification, where immunoglobulins are bound by those proteins at physiologic pH and then released from the proteins by lowering the pH. When serum, plasma, or whole blood samples are used, a sample, such as a 10-250 µl sample (e.g., a 20 µl sample), can be directly subjected to Melon Gel, Protein A, Protein or Protein L purification. Size exclusion principles such as a TurboFlow column can also be employed to separate the non-immunoglobulin contaminants from a sample. When urine samples are used, a urine sample can be buffered, e.g., a 50 µl urine sample can be diluted first with 50 µl of 50 mM ammonium bicarbonate.

Intact immunoglobulins can be further processed to decouple the light chains in a total immunoglobulin sample from the heavy chain immunoglobulins. Decoupling can be achieved by treating the total immunoglobulins with a reducing agent, such as DTT (2,3 dihydroxybutane-1,4-dithiol), DTE (2,3 dihydroxybutane-1,4-dithiol), thioglycolate, cysteine, sulfites, bisulfites, sulfides, bisulfides, TCEP (tris(2-carboxyethyl)phosphine), 2-mercaptoethanol, and salt forms thereof. In some cases, the reducing step is performed at elevated temperature, e.g., in a range from about 30° C. to about 65° C., such as about 55° C., in order to denature the proteins. In some cases, the sample is further treated, e.g., by modifying the pH of the sample or buffering the sample. In some cases, the sample can be acidified. In some cases, the sample can be neutralized (e.g., by the addition of a base such as bicarbonate).

In some cases, the antigen binding fragments (Fab) of immunoglobulins can be cleaved from the intact immunoglobulins using proteases such as pepsin. Excess reagents and salts can be removed from the samples using methods known to those having ordinary skill in the art.

Mass Spectrometry Methods

The materials and methods for identifying and monitoring immunoglobulin cleavage (e.g., IgG cleavage) described herein can include any appropriate mass spectrometry (MS) technique. After sample preparation, a sample can be subjected to a MS technique, either directly or after separation on a high performance liquid chromatography column (HPLC). In some cases, liquid chromatography mass spectrometry (LC-MS) can be used to analyze the mass spectrum of the ions. For example, the method can be used to identify multiply charged ions (e.g., the +1 ions, +2 ions, +3 ions, +4 ions, +5 ions, +6 ions, +7 ions, +8 ions, +9 ions, +10 ions, +11 ions, +12 ions, +13 ions, +14 ions, +15 ions, +16 ions, +17 ions, +18 ions, +19 ions, +20 ions, +21 ions, and +22 ions), resulting from the IgG cleavage fragments in the sample. In some cases, the +22 charged ion is identified and used for further analysis. In some cases, the samples are not fragmented during the mass spectrometry technique. LC-MS is an analytical technique that combines the physical separation capabilities of liquid chromatography with the mass analysis capabilities of mass spectrometry, and is suitable for detection and potential identification of chemicals in a complex mixture. Any LC-MS instrument can be used, e.g., the ABSciex 5600 Mass Spectrometer. In some cases, microflowLC-MS can be utilized. Any suitable microflow instrument can be used, e.g., the Eksigent Ekspert 200 microLC. The ion mass spectrum can be analyzed for one or more peaks corresponding to one or more IgG cleavage fragments in the sample. For example, one or more ion peaks, e.g., a +22 ion peak, can be examined to determine the IgG cleavage fragments in the sample.

In some cases, electrospray ionization coupled to a quadrupole time-of-flight mass spectrometry (ESI-Q-TOF MS) can be used to analyze the mass spectrum of a sample, e.g., the mass spectrum of the +22 charge state of the IgG cleavage fragments in the sample. Electrospray ionization mass spectrometry (ESI MS) is a useful technique for producing ions from macromolecules because it overcomes the propensity of these molecules to fragment when ionized. In addition, ESI often produces multiply charged ions, effectively extending the mass range of the analyzer to accommodate the orders of magnitude observed in proteins and other biological molecules. A quadrupole mass analyzer (Q) consists of four cylindrical rods, set parallel to each other. In a quadrupole mass spectrometer, the quadrupole is the component of the instrument responsible for filtering sample ions based on their mass-to-charge ratio (m/z). The time-of-flight (TOF) analyzer uses an electric field to accelerate the ions through the same potential, and then measures the time they take to reach the detector. If the particles all have the same charge, the kinetic energies are identical, and their velocities depend only on their masses. Lighter ions reach the detector first. Any ESI-Q-TOF mass spectrometer can be used, e.g., the AB Sciex TripleTOF 5600 quadrupole time-of-flight mass spectrometer. The mass spectrum, e.g., the mass spectrum of multiply charged intact light chain or heavy chain polypeptide ions, can be analyzed to identify one or more peaks at an appropriate mass/charge expected for the chain. For example, for the IgG cleavage fragments, the peaks can occur at about 600-2500 m/z. In some cases, the peaks can occur at about 700-2000 m/z (e.g., about 800-1600 m/z for the +22 ion).

The multiply charged ion peaks can be converted to a molecular mass using known techniques. For example, multiply charged ion peak centroids can be used to calculate average molecular mass and the peak area value used for quantification is supplied by a software package. Specifically, multiple ion deconvolution can be performed using the Bayesian Protein Reconstruct software package in the BioAnalyst companion software package in ABSCIEX Analyst TF 1.6. Deconvoluted and multiply charged ions can also be manually integrated using the Manual Integration 33 script in Analyst TF. Providing the molecular mass for the IgG cleavage fragments in the sample facilitates sequencing and identification of the IgG cleavage fragments in the sample. For example, the methods provided herein can be used to identify plasmin-generated IgG cleavage fragments in the sample. In addition, the methods provided herein can be used to compare the relative abundance of the IgG cleavage fragments as compared to a control or reference sample. As described herein, the plasmin-generated IgG cleavage can include the N-terminal amino acid sequence THTCPPCPA-PEL (SEQ ID NO:2). The presence or absence of this plasmin-generated IgG cleavage fragment can be indicative of activation of complement and therefore is a useful tool for diagnosing and monitoring patients with an inflammatory condition (e.g., an immune disease or an infection).

In some cases, matrix assisted laser adsorption ionization-time of flight mass spectrometry (MALDI-TOF MS) can be used to analyze the mass spectrum of a sample. MALDI-TOF MS identifies proteins and peptides as mass charge (m/z) spectral peaks. Further, the inherent resolution of MALDI-TOF MS allows assays to be devised using multiple affinity ligands to selectively purify/concentrate and then analyze multiple proteins in a single assay.

Methods for Screening Samples and for Diagnosing and Monitoring Inflammatory Conditions The materials and methods provided herein can be used for identifying and monitoring immunoglobulin cleavage (e.g., IgG cleavage).

In some cases, the mass spectrometry based methods disclosed herein can be used to screen a sample (e.g., a biological sample) for a particular IgG cleavage fragment (e.g., plasmin-generated IgG cleavage fragments). For example, the mass spectrometry based methods disclosed herein can be used for detecting an IgG cleavage in a sample from a patient. For example, the mass spectrometry based methods disclosed herein can be used for identifying plasmin activation in a sample from a patient, for detecting complement activation in a patient. For example, the mass spectrometry based methods disclosed herein can be used for diagnosing an inflammatory condition in a patient. The mass spectrometry based methods disclosed herein can include subjecting a sample having one or more immunoglobulins to a mass spectrometry assay. The sample can be pretreated to isolate or enrich immunoglobulins present in the sample. The immunoglobulin light chains can be decoupled from the immunoglobulin heavy chains prior to the mass spectrometry analysis. The spectrum obtained from the assay can then be used to identify IgG cleavage fragments in the sample. In some cases, the relative abundance of identify IgG cleavage fragments can be determined by converting the peak areas of one or more of the identified peaks into a molecular mass.

The presence or absence of a particular IgG cleavage fragment (e.g., plasmin-generated IgG cleavage fragments) can be used to diagnose an inflammatory condition. An inflammatory condition can affect any part of the patient. For example, an inflammatory condition disease can affect a major organ (e.g., heart, kidney, liver, lung, and skin), glands (e.g., adrenal, pancreas, thyroid, salivary, and multi-glandular), reproductive organs, digestive system, blood, connective tissue, muscle, nervous system, vascular system, eyes, and/or ears. An inflammatory condition can be an immune disease or an infection (e.g., a pathogenic infection). The presence of plasmin-generated IgG cleavage fragments can indicate that the inflammatory condition may be an autoimmune disease. An immune disease can be an autoimmune disease or an immune deficiency. Examples of autoimmune diseases include, without limitation, Barraquer-Simons Syndrome, asthma, lupus erythematosus, glomerulonephritis, various forms of arthritis (e.g., rheumatoid arthritis), autoimmune heart disease, multiple sclerosis, inflammatory bowel disease, vasculitis, paroxysmal nocturnal hemoglobinuria, and Sjögren's syndrome. In some cases, the presence of a plasmin-generated IgG cleavage fragment can be used to diagnose lupus erythematosus, rheumatoid arthritis, multiple sclerosis, Sjögren's syndrome, inflammatory bowel disease, or vasculitis. Examples of immune deficiencies include, without limitation, humoral immune deficiency, T cell deficiency, granulocyte deficiency, asplenia, complement deficiency, severe combined immunodeficiency, and acquired immune deficiency syndrome. The absence of plasmin-generated IgG cleavage fragments can indicate that the inflammatory condition may be an infection. An infection can be caused by any appropriate pathogen (e.g., bacteria, viruses, or fungi). In some cases, the presence or absence of plasmin-generated IgG cleavage fragments can be used to distinguish between inflammation associated with an autoimmune disease and inflammation associated with an infection. In some cases, the methods provided herein can be used to confirm a diagnosis made by current methods such as gel electrophoresis. For example, if a negative result is obtained from gel electrophoresis, the present methods can be used as a secondary test to confirm or counter such results. In some cases, the diagnosis provided herein can be confirmed using such standard methods.

In some cases, the mass spectrometry based methods provided herein can also be used for monitoring a patient. For example, the mass spectrometry based methods disclosed herein can be used for monitoring plasmin activation in a patient. For example, the mass spectrometry based methods disclosed herein can be used for monitoring treatment of an immune disease in a patient. The mass spectrometry based methods disclosed herein can include providing a first sample and a second sample of the subject. For example, the mass spectrometry based methods disclosed herein can include providing a first sample of the subject before the treatment and a second sample of the subject during or after the treatment. The first and second samples can be pretreated to isolate or enrich immunoglobulins present in the first and second samples. The immunoglobulin light chains in the first and second samples can be decoupled from the immunoglobulin heavy chains prior to the mass spectrometry analysis. The spectrum obtained from the assay can then be used to identify IgG cleavage fragments in the first and second samples. In some cases, the relative abundance of identify IgG cleavage fragments in the first and second samples can be determined by converting the peak areas of one or more of the identified peaks into a molecular mass. The presence or absence of a particular IgG cleavage fragment (e.g., a plasmin-generated IgG cleavage fragment) can be determined in the first and second samples. A decrease (or loss) of the amount of plasmin-generated IgG cleavage fragments indicates that the plasmin activation in the patient has been reduced (or eliminated); while an increase in the amount of plasmin-generated IgG cleavage fragments indicates that plasmin activation in the patient has increased. In cases where a first sample of the subject is before the treatment and a second sample of the subject is during or after the treatment, the presence or absence of a plasmin-generated IgG cleavage fragment is determined before and after the treatment and compared. A decrease (or loss) of the amount of plasmin-generated IgG cleavage fragments indicates that the treatment may be effective for the subject; while an increase or no change in the amount of plasmin-generated IgG cleavage fragments indicates that the treatment may be ineffective for the subject. For example, the amount of IgG cleavage fragment in a first sample and in a second sample can be determined, and the amount of IgG cleavage fragment in the first sample can be compared to the amount of IgG cleavage fragment and the second sample. For example, the concentration of IgG cleavage fragment in a first sample and in a second sample can be determined, and the concentration of IgG cleavage fragment in the first sample can be compared to the amount of IgG cleavage fragment and the second sample.

The invention will be further described in the following examples, which do not limit the scope of the invention described in the claims.

EXAMPLES

Figure 2:
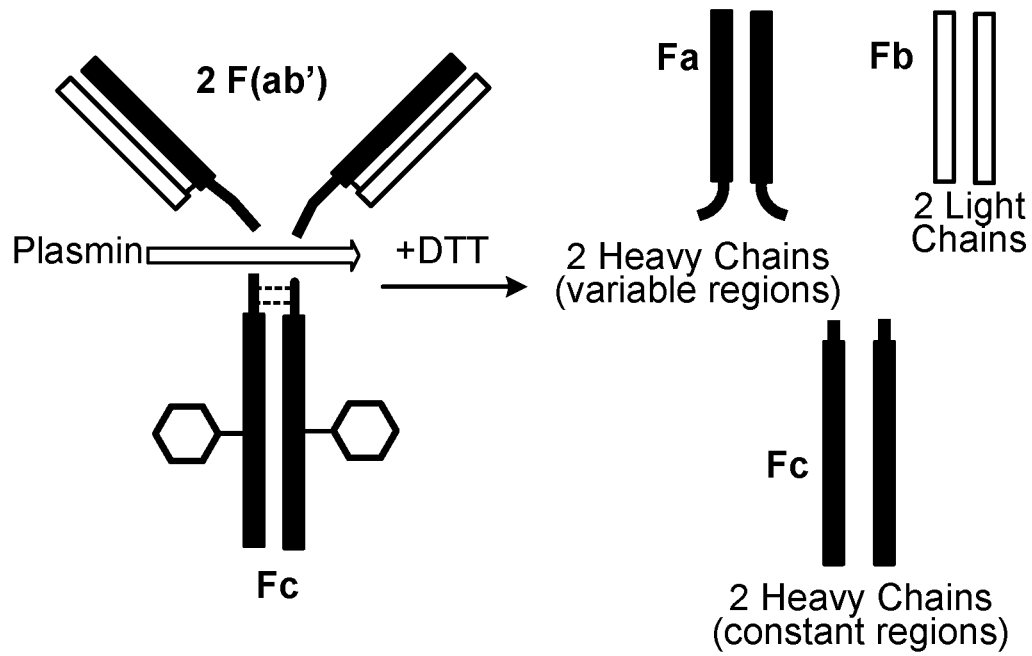
FIG. 2 is a schematic model of an IgG immunoglobulin after cleavage with plasmin and the heavy chain and light chain fragments generated when reduced with DTT.

Example 1: Mass Spectrometry to Identify IgG Fc and Fab Fragments Produced by Plasmin in Patient Serum Immunoglobulins of the IgG isotype can be cleaved by enzymes such as IdeS and plasmin. A model of an IgG immunoglobulin with a close up of the heavy chain amino acid sequence (SEQ ID NO:1) in the hinge region where plasmin and IdeS cleave the molecule into Fc and F(ab') or F(ab')2 fragments is shown in FIG. 1. Cleavage of an IgG with these enzymes generates fragments referred to as the Fc portion (which contains the constant region of the heavy chain) and the Fab or F(ab')2 portion (which contains the variable region of the heavy chain along with the entire light chain) as shown in FIG. 2. The expected molecular masses for Fa, Fb, and Fc fragments from IgG1 in serum are 25,000 Da-26,000 Da, 22,500 Da-24,800 Da, and 25,304 Da+glycosylation, respectively. These IgG fragments have usually been monitored by low resolution gel electrophoresis.

Plasmin is usually associated with the breakdown of fibrin clots. However, IgG cleavage in vivo by plasmin is associated with activation of the complement system via Fc fragments. Here, the accurate molecular mass of Fc and Fab fragments coupled with top-down MS was used to identify plasmin activity in patient serum.

Methods

The Fc and Fab portions of plasmin cleaved IgG were identified by LC retention time, accurate molecular mass, and top-down MS.

Sample Prep:

A volume of 20 µL of serum was enriched for immunoglobulins using 180 µL of Melon Gel following the manufacturer's instructions. After immunoglobulin enrichment 20 µL of sample was reduced by adding 20 µL of 100 mM DTT and 20 µL of 50 mM ammonium bicarbonate then incubated at 55° C. for 30 minutes. Ides enzyme was purchased from Promega and used as directed.

LC Method:

An Eksigent Ekspert 200 microLC was used for separation; mobile phase A consisted of water+0.1% FA, and mobile phase B consisted of 90% acetonitrile+10% 2-propanol+0.1% FA. A 2 µL injection was made onto a 1.0×75 mm Poroshell 300SB-C3 column with 5 µm particle size flowing at 25 µL/minute while the column was heated at 60° C. A 25 minute gradient starting at 80% A 20% B was used.

ESI-Q-TOF MS:

Spectra were collected on an ABSciex Triple-TOF 5600 quadrupole time-of-flight mass spectrometer (SCIEX, ON,CA) run in ESI positive mode with a Turbo V dual ion source Source conditions were: IS: 5500, Temp: 500, CUR: 45, GS1: 35, GS2: 30, CE: 50±5. TOF MS scans were acquired from m/z 600-2500 with an acquisition time of 100 ms. Data Analysis: Analyst TF v1.6 was used for instrument control. Data were viewed using Analyst TF v1.6 and PeakView v1.2.0.3. Deconvolution of multiply charged light chain ions was done using the Bayesian Protein Reconstruct program in BioAnalyst.

Results

Figure 3C:
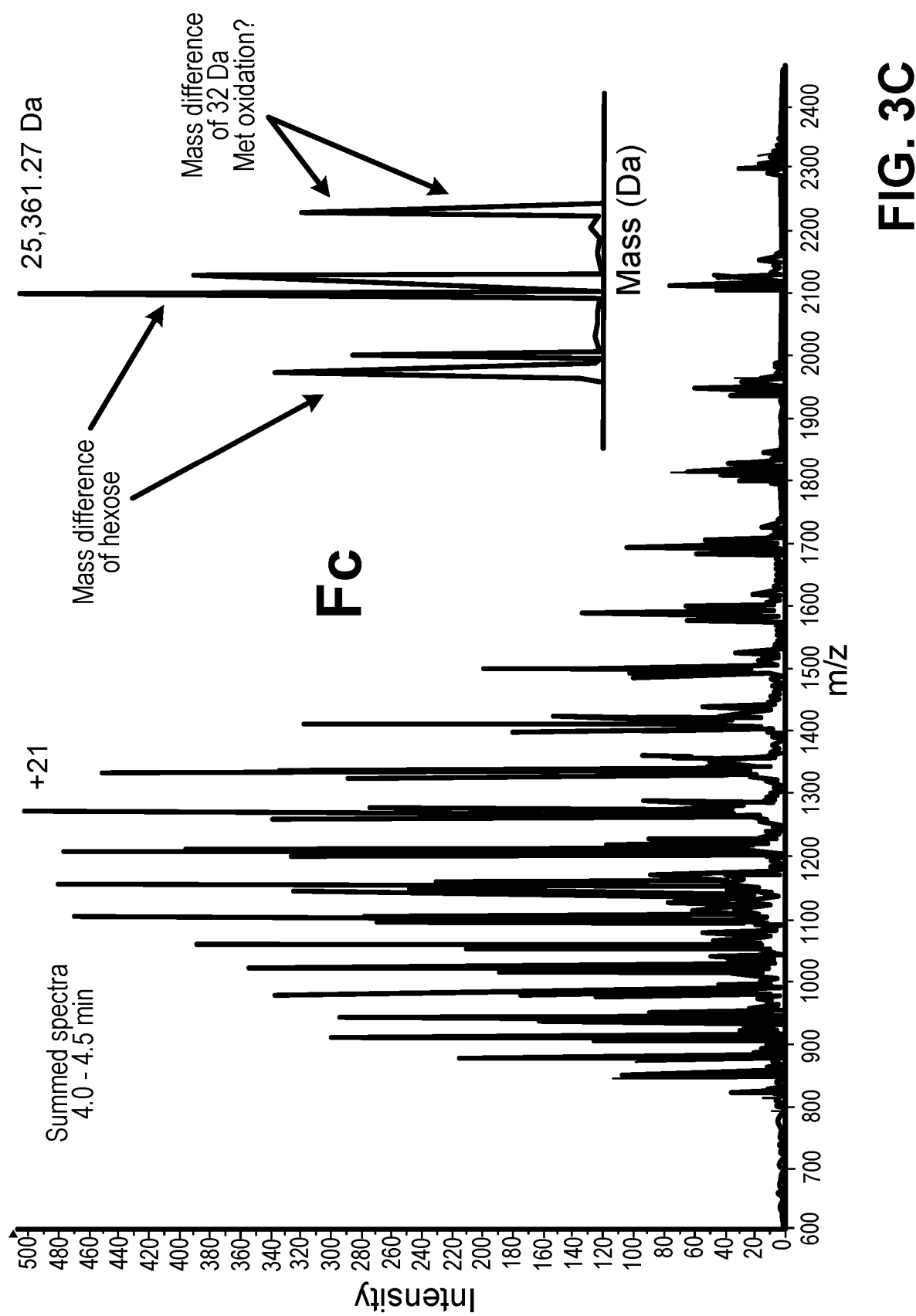
FIG. 3 contains MS spectrum of IdeS cleaved serum. A) A total ion chromatogram (TIC) from pooled normal human serum polyclonal immunoglobulins. B) A TIC from pooled normal human serum polyclonal immunoglobulins with cleavage using IdeS enzyme. C) A summed mass spectrum of a deconvoluted mass spectrum (inset) from retention times for the Fc fragment. D) Close up charge states for the polyclonal Fa and Fb fragments.

IdeS cleaved serum was analyzed by MS (FIG. 3). Analysis of a large set of serum samples revealed patients with IgG related proteins in their sera having LC retention times, ESI charge state distributions, and molecular masses similar to those observed in IgG cleaved with the enzyme IdeS. Further investigation into the origin of these proteins led to the finding that their accurate molecular mass was the same as that expected from the cleavage of IgG by the endogenous serine protease plasmin (FIG. 4). A summed mass spectra for serum with suspected plasmin cleavage (FIG. 4B) are similar to spectra observed for normal serum treated with IdeS (FIG. 3C). The most abundant peak in the IdeS Fc spectrum and the patient's spectrum differ by the molecular mass of the amino acids between the cleavage sites of plasmin and IdeS.

Figure 3D:
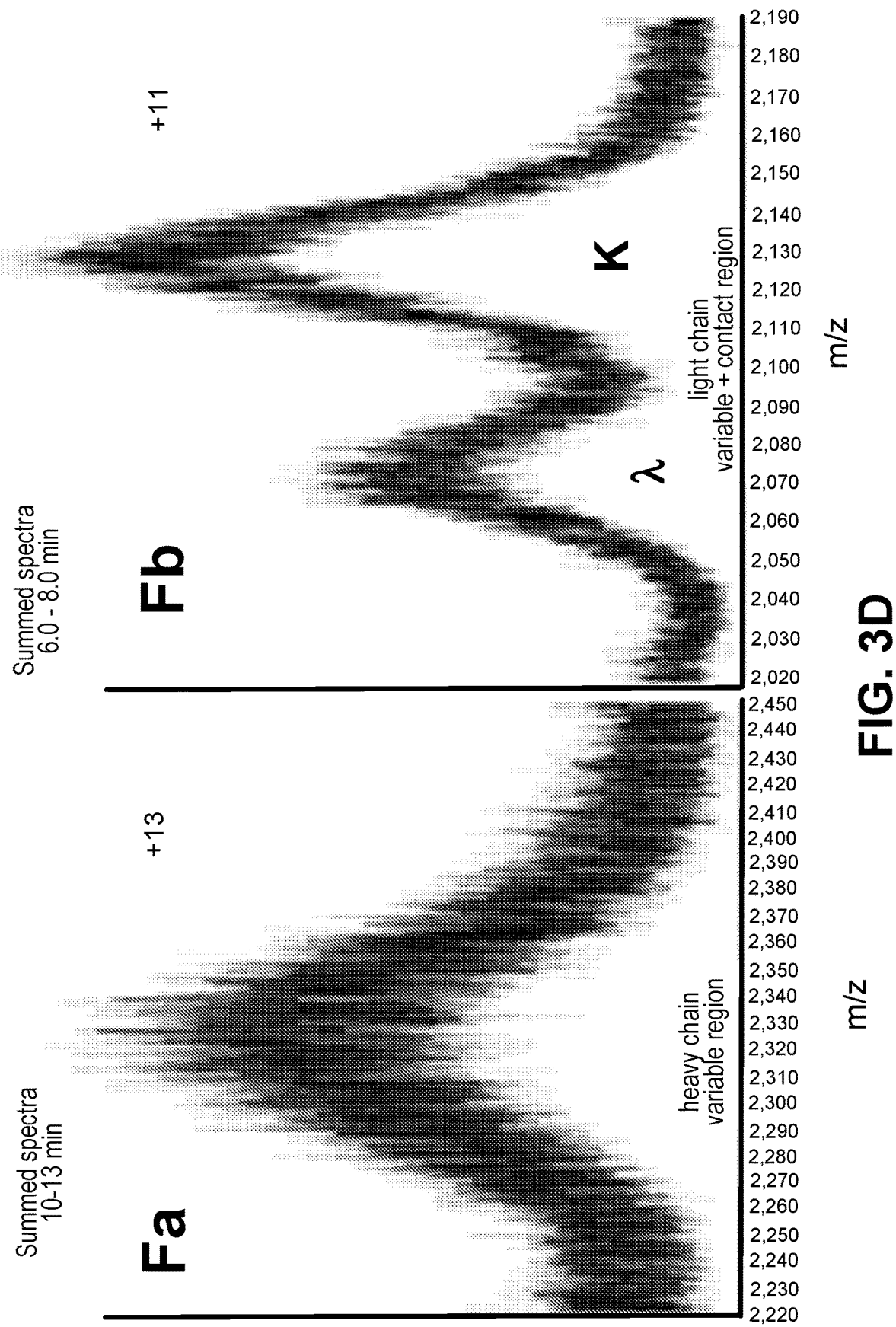
Figure 5:
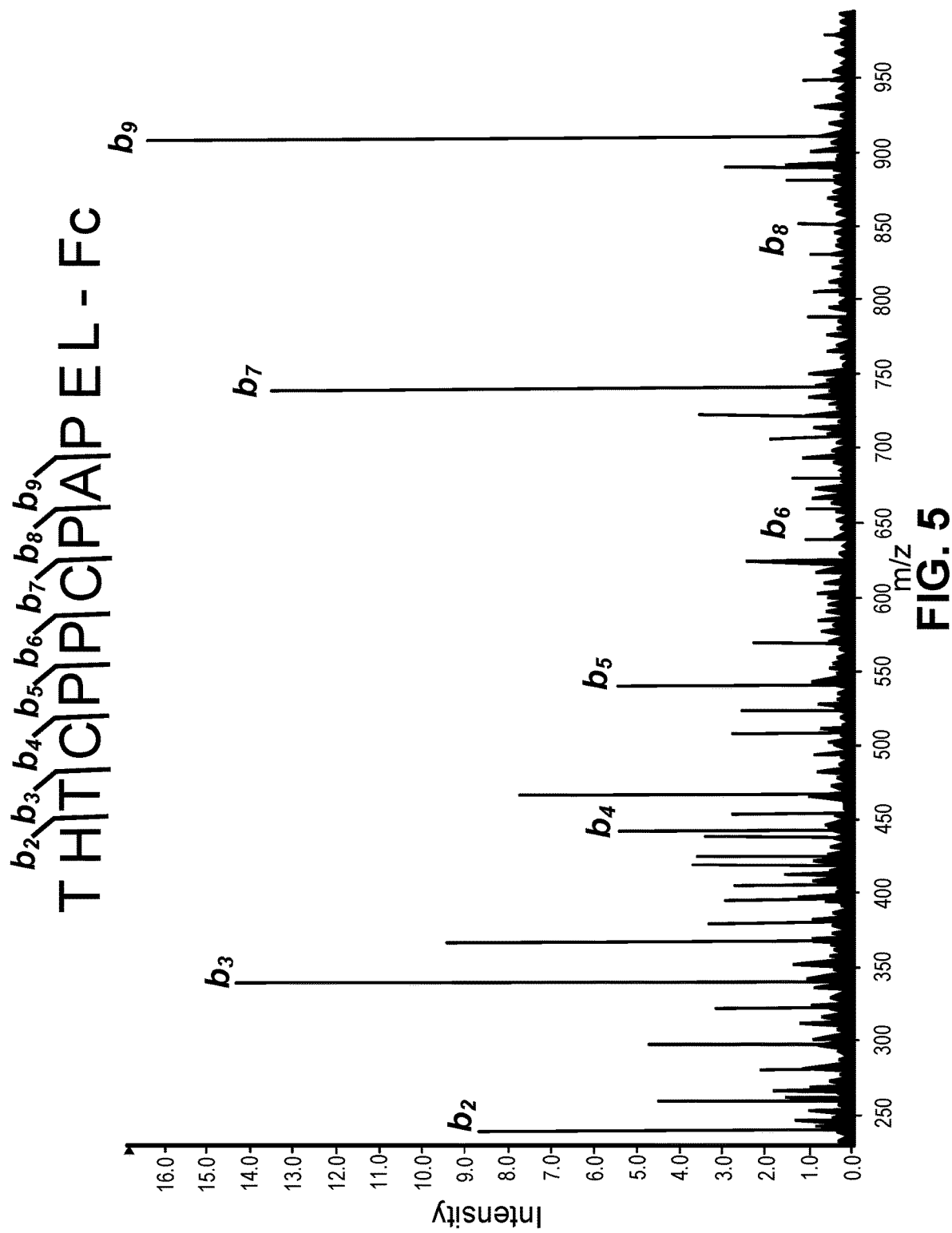
FIG. 5 is a top-down mass spectrum of the +22 charge state from the presumed plasmin cleaved Fc fragment (SEQ ID NO:2).
Figure 6:
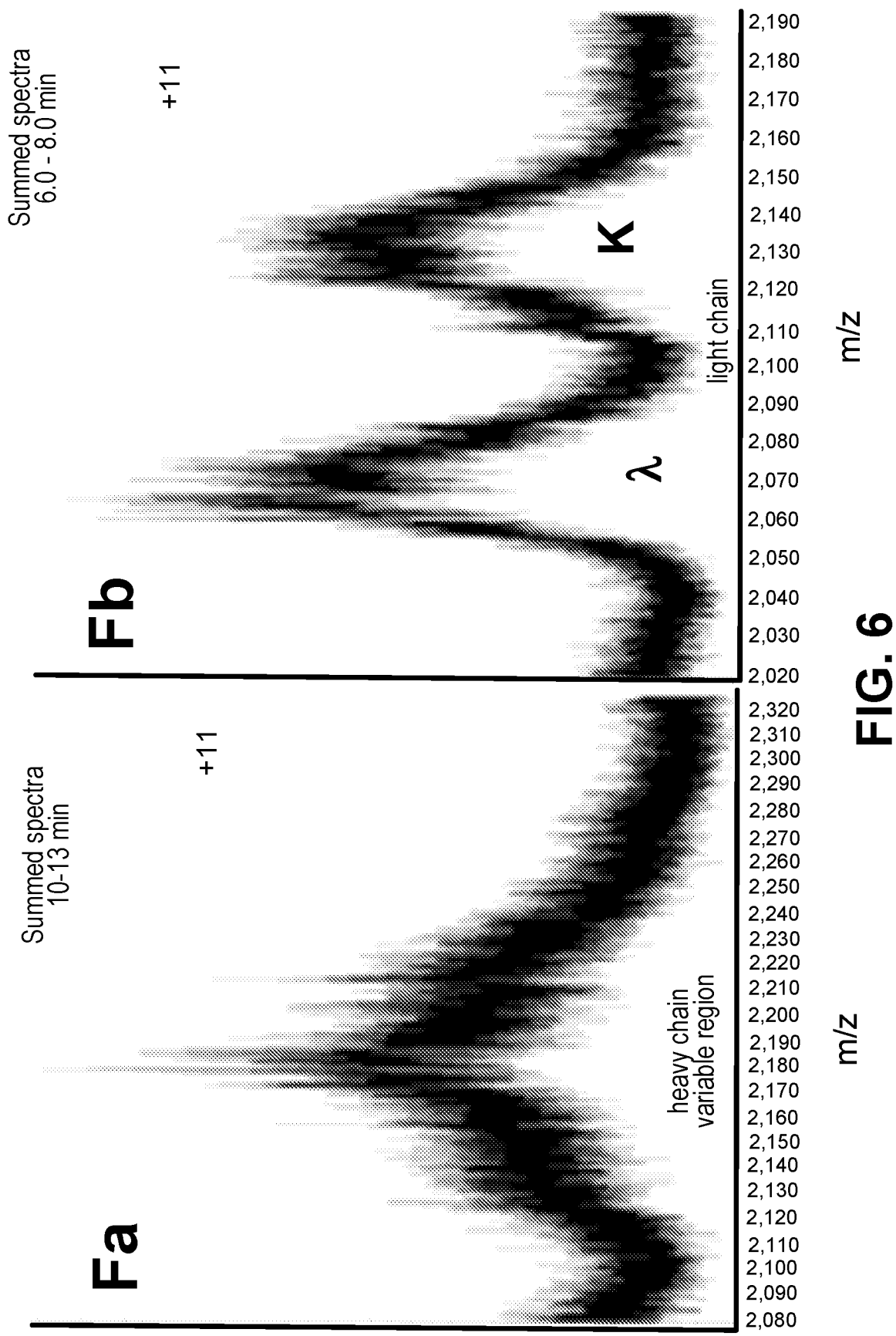
FIG. 6 contains a summed mass spectrum from retention times for the polyclonal Fa and Fb fragments showing the molecular mass distributions for the +11 charge states from the patient with plasmin IgG cleavage.

The sequence of the presumed Fc fragments in FIG. 4 was confirmed as THTCPPCPAPEL (SEQ ID NO:2) using top-down MS (FIG. 5). The b-ions observed confirm that plasmin generated the IgG Fc fragments in this patient's serum. A summed mass spectra for patient serum with plasmin cleavage (FIG. 6) differs from spectra observed for normal serum treated with IdeS (FIG. 3D). The different distributions represent the patient's individual variable region repertoire for heavy chains and light chains. The Fa portions of the plasmin generated fragments containing the IgG heavy chain variable region had a single molecular mass distribution consistent with the observation that the Fb portion containing the light chain had both kappa and lambda isotype distributions (FIG. 6).

Figure 7:
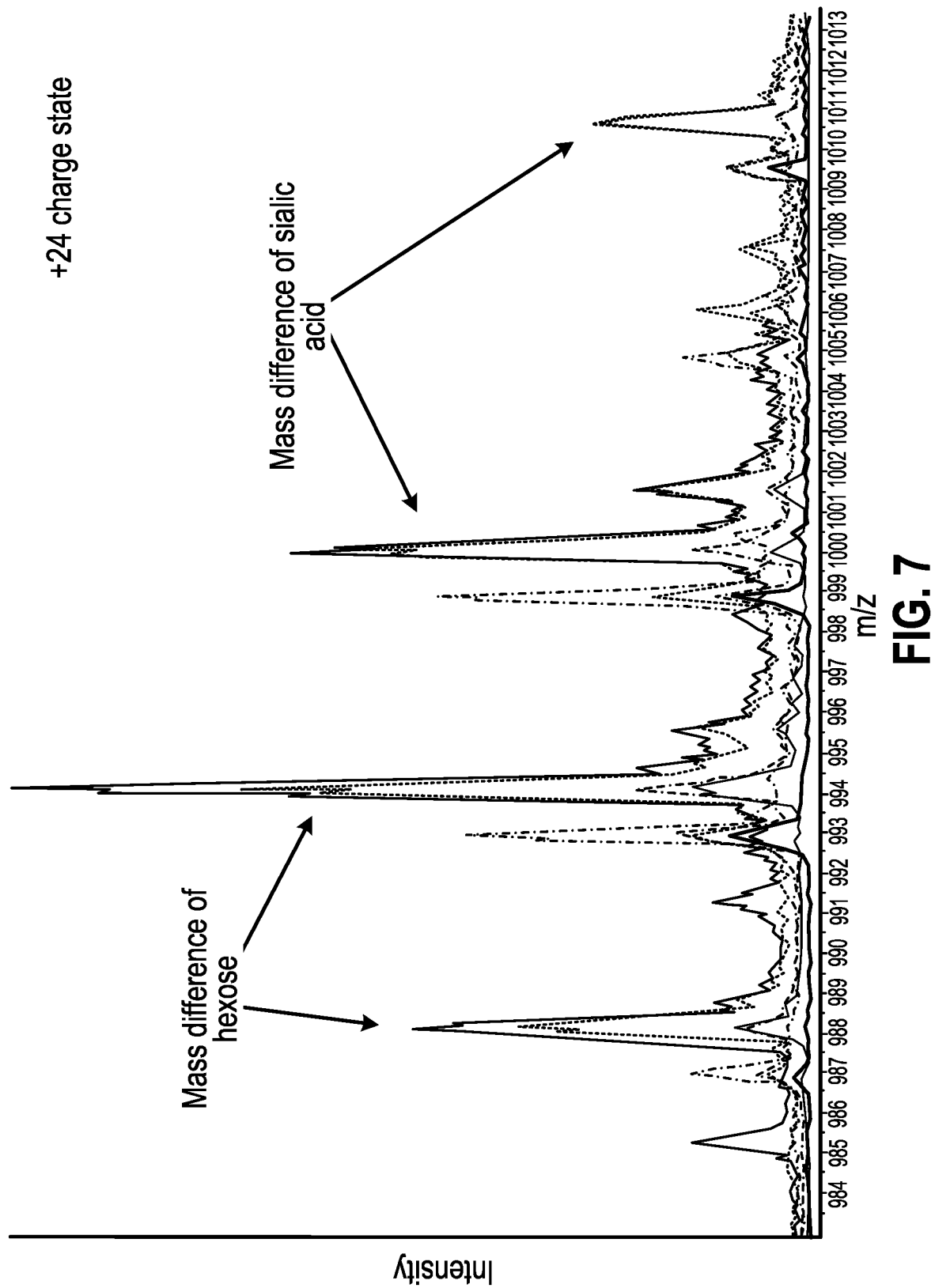
FIG. 7 shows an overlay of summed spectra from the Fc retention time taken from 6 different patients with evidence for plasmin IgG cleavage.

Multiple patient sera with the same Fc fragments were overlaid (FIG. 7), and were found to have identical top-down MS spectra demonstrating that plasmin enzymatic activity was conserved. The overlay also illustrates the ability of the mass spectrometer to readily identify different Fc glycoforms present in each individual patient.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method for detecting endogenous IgG cleavage in a patient, the method comprising:
   a. providing a sample comprising IgG from the patient, wherein the sample is a blood sample;
   b. subjecting the sample to a mass spectrometry technique to obtain a mass spectrum of the sample; and
   c. identifying the presence of an endogenous IgG cleavage fragment in said sample, wherein the IgG cleavage fragment is a plasmin generated IgG cleavage fragment.

2. The method of claim 1, wherein the sample is suspected to comprise plasmin IgG cleavage.

3. The method of claim 1, wherein the blood sample is a serum sample.

4. The method of claim 1, wherein the patient is a human.

5. The method of claim 1, wherein the IgG cleavage fragment comprises the amino acid sequence THTCPPCPAPEL (SEQ ID NO:2).

6. The method of claim 5, wherein the IgG cleavage fragment is glycosylated.

7. The method of claim 1, wherein the IgG cleavage fragment is from a polyclonal IgG.

8. The method of claim 1, wherein the IgG cleavage fragment is from a monoclonal IgG.

9. The method of claim 1, further comprising isolating the IgG from the sample.

10. The method of claim 1, further comprising enriching the IgG from the sample.

11. The method of claim 1, further comprising contacting the sample with a reducing agent prior to subjecting the sample to the mass spectrometry technique.

12. The method of claim 11, wherein the reducing agent is dithiothreitol (DTT).

13. The method of claim 1, wherein the mass spectrometry technique is electrospray ionization mass spectrometry (ESI-MS).

14. The method of claim 13, wherein the ESI-MS technique comprises a quadrupole time-of-flight (TOF) mass spectrometer.

15. The method of claim 14, wherein the mass spectrometry technique is a top-down mass spectrometry technique.

16. The method of claim 1, wherein the IgG cleavage fragment is an Fc fragment.

17. The method of claim 1, wherein the IgG cleavage fragment is glycosylated.

* * * * *

SEQUENCE LISTING

<160> NUMBER OF SEQ ID NOS: 3

<210> SEQ ID NO 1

<211> LENGTH: 22
<212> TYPE: PRT
<213> ORGANISM: Homo sapiens

<400> SEQUENCE: 1

Pro Lys Ser Cys Asp Lys Thr His Thr Cys Pro Pro Cys Pro Ala Pro
1               5                   10                  15

Glu Leu Leu Gly Gly Pro
            20

<210> SEQ ID NO 2
<211> LENGTH: 12
<212> TYPE: PRT
<213> ORGANISM: Homo sapiens

<400> SEQUENCE: 2

Thr His Thr Cys Pro Pro Cys Pro Ala Pro Glu Leu
1               5                   10

<210> SEQ ID NO 3
<211> LENGTH: 227
<212> TYPE: PRT
<213> ORGANISM: Homo sapiens

<400> SEQUENCE: 3

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Lys
225